(12) United States Patent
Kawahara et al.

(10) Patent No.: US 10,687,700 B2
(45) Date of Patent: Jun. 23, 2020

(54) VISUAL FIELD MEASURING METHOD, VISUAL FIELD MEASURING APPARATUS, AND OPTOTYPE

(71) Applicant: NATIONAL UNIVERSITY CORPORATION EHIME UNIVERSITY, Matsuyama-shi, Ehime (JP)

(72) Inventors: Minoru Kawahara, Matsuyama (JP); Nobuyuki Takahashi, Matsuyama (JP)

(73) Assignee: NATIONAL UNIVERSITY CORPORATION EHIME UNIVERSITY, Matsuyama-shi, Ehime (JP)

(*) Notice: Subject to any disclaimer, the term of this patent is extended or adjusted under 35 U.S.C. 154(b) by 212 days.

(21) Appl. No.: 15/750,179

(22) PCT Filed: Aug. 2, 2016

(86) PCT No.: PCT/JP2016/072647
§ 371 (c)(1),
(2) Date: Feb. 3, 2018

(87) PCT Pub. No.: WO2017/022757
PCT Pub. Date: Feb. 9, 2017

(65) Prior Publication Data
US 2018/0296084 A1 Oct. 18, 2018

(30) Foreign Application Priority Data
Aug. 3, 2015 (JP) .................... 2015-153722

(51) Int. Cl.
*A61B 3/024* (2006.01)
*A61B 3/032* (2006.01)
*A61B 3/00* (2006.01)

(52) U.S. Cl.
CPC ........... *A61B 3/024* (2013.01); *A61B 3/0025* (2013.01); *A61B 3/0033* (2013.01); *A61B 3/0041* (2013.01); *A61B 3/032* (2013.01)

(58) Field of Classification Search
CPC ....... A61B 3/024; A61B 3/032; A61B 3/0033; A61B 3/0041; A61B 3/0025
See application file for complete search history.

(56) References Cited

U.S. PATENT DOCUMENTS

2005/0083485 A1* 4/2005 Toshima ............. A61B 3/0033
351/239
2011/0027766 A1* 2/2011 Yoo ..................... A61B 3/032
434/262

(Continued)

FOREIGN PATENT DOCUMENTS

CN 1612709 A 5/2005
JP H07-313457 A 12/1995

(Continued)

OTHER PUBLICATIONS

Extended European Search Report (EESR) dated Jul. 8, 2019 in EP Patent Application No. 16833036.3, which is the EP counterpart of the present application.

(Continued)

*Primary Examiner* — Cara E Rakowski
(74) *Attorney, Agent, or Firm* — JTT Patent Services, LLC; Gerald T. Peters

(57) ABSTRACT

A method for measuring visual field comprising a reference standardized symbol display operation in which a standardized test symbol is displayed at a reference location BP provided at a center of a display 2; a reference input operation in which a test subject is made to input the fact that the standardized test symbol displayed at the reference standardized symbol display operation has been recognized; a peripheral standardized symbol display operation in (Continued)

which, following input of the fact that the standardized test symbol was recognized at the reference input operation, a standardized test symbol is displayed at a location different from the reference location BP; and a peripheral input operation in which the test subject is made to input the fact that the standardized test symbol displayed at the peripheral standardized symbol display operation has been recognized; wherein a response time is measured from when the standardized test symbol is displayed at the peripheral standardized symbol display operation to when the fact that the standardized test symbol has been recognized is input at the peripheral input operation.

16 Claims, 13 Drawing Sheets

(56) References Cited

U.S. PATENT DOCUMENTS

| | | | |
|---|---|---|---|
| 2015/0190048 | A1 | 7/2015 | Huang |
| 2016/0220162 | A1* | 8/2016 | Mantysalo ............. A61B 3/024 |

FOREIGN PATENT DOCUMENTS

| | | | |
|---|---|---|---|
| JP | 2002-000565 | A | 1/2002 |
| JP | 2002-172089 | A | 6/2002 |
| JP | 2002-315725 | A | 10/2002 |
| JP | 2015-6425 | A | 1/2005 |
| JP | 2005-102947 | A | 4/2005 |
| JP | WO2003/057021 | A1 | 5/2005 |
| JP | 2007-20788 | A | 2/2007 |
| WO | 2003/057021 | A1 | 7/2003 |
| WO | 2015/028721 | A1 | 3/2015 |

OTHER PUBLICATIONS

Jan Dolderer et al: "Scotoma mapping by semi-automated kinetic perimetry: the effects of stimulus properties and the speed of subjects' responses : Acta Opthalmologica Scandinavica 2006", Acta Ophthalmologica Scandinavica, vol. 84, No. 3, Jun. 1, 2006, pp. 338-344, XP055571403, DK ISSN: 1395-3907, DOI: 10.1111/I.1600-0420.2005.00624.x. EESR (NPL Cite No. 1) cites abstract; figures 1, 2; p. 339.

Peggel Dorothe A et al: "The Tolz Temporal Topography Study: Mapping the visual field across the life span. Part I: The topography of light detection and temporal-information processing", Attention, Perception, & Psychophysics, New York, NY : Springer, Boston, vol. 74, No. 6, Apr. 7, 2012, pp. 1114-1132, XP036257816, ISSN: 1943-3921, DOI: 10.3758/S13414-012-0278-Z [retrieved on Apr. 7, 2012]. EESR (NPL Cite No. 1) cites abstract; figs. 1, 2; p. 1119, left-hand column, last paragraph—p. 1119, right-hand column, paragraph first.

Japanese-language web page entitled "Visual inspection_ important for early detection of glaucoma without initial symptoms" downloaded by undersigned from http://medical-checkup.info/article/43671142.html on Apr. 26, 2018, believed to be representative of content available at same website before priority date of present application.

Japanese-language web page entitled "The Japanese Ophthalmologist Society_ Eye Disease Glaucoma.html" downloaded by undersigned from http://www.nichigan.or.jp/public/disease/ryokunai_ryokunai.jsp on Apr. 26, 2018, believed to be representative of content available at same website before priority date of present application.

Office Action dated Jan. 19, 2020 in CN Patent Application No. 2016800447741, which is the Chinese counterpart of the present application.

* cited by examiner

FIG. 5

Right eye (A)

Both eyes (B)

Right eye (A)

Both eyes (B)

(A)

(B)

Scotoma (Marriotte blind spot) determination region (A)

(B)

(A)

(B)

VISUAL FIELD MEASURING METHOD, VISUAL FIELD MEASURING APPARATUS, AND OPTOTYPE

CROSS-REFERENCE TO RELATED APPLICATION, PRIORITY CLAIM, AND INCORPORATION BY REFERENCE

This application is the national stage of International Application No. PCT/JP2016/072647, entitled "Visual Field Measuring Method, Visual Field Measuring Apparatus, and Optotype", filed 2 Aug. 2016; and claims benefit of priority under 35 USC 119(a)-(d) to Japanese Patent Application No. 2015-153722, entitled "Visual Field Measuring Method, Visual Field Measuring Apparatus, and Optotype"; filed 3 Aug. 2015, the contents of both of which applications are incorporated herein in their entireties by reference.

TECHNICAL FIELD

The present invention relates to a visual field measuring method, visual field measuring apparatus, and optotype. More specifically, it is related to a visual field measuring method capable of being used to test for any of a variety of diseases and/or the degree to which any of various respective diseases has progressed, to a visual field measuring apparatus that embodies this visual field measuring method, and to an optotype capable of being used to measure that type of visual acuity which is minimum separable acuity.

BACKGROUND ART

In the field of therapeutic ophthalmology, testing of visual performance plays an important role for obtaining an objective assessment when seeking to grasp the pathology of eye disease, make decisions regarding treatment strategy, verify the effect of treatment, and so forth. In general, visual performance subject to testing includes visual acuity, visual field, color perception, and other such measures of the performance with which visual information is input from the eye.

While testing of visual acuity is regularly carried out as an example of such visual performance, a broader definition of visual acuity would be the ability to recognize that a thing is present and to distinguish what it is (perception of form). This visual acuity (perception of form) is divided into four categories, these being "minimum perceptible acuity," "minimum separable acuity," "minimum legible acuity," and "vernier acuity." When measuring visual acuity, it is ordinarily "minimum separable acuity" that is measured.

To measure this "minimum separable acuity," Landolt rings are typically used. A Landolt ring is of such shape that a notch is provided at a portion of a donut-like ring, minimum separable acuity being measured based on whether or not presence of this notch can be recognized. More specifically, a test subject is shown Landolt rings of differing size, and the size required for the test subject to be able to recognize the location of the notch is ascertained. Having done this, the size of the gap at the notch of the Landolt ring of the smallest size for which the location of the notch can be recognized can be taken to be the minimum separable acuity of the test subject.

Furthermore, testing of visual field is carried out to investigate any of a variety of diseases and/or the degree to which any of various respective diseases has progressed, such diseases including glaucoma, pigmentary degeneration of the retina, diabetic retinopathy, detachment of the retina, and macular degeneration. During such visual field testing, a perimeter is used to measure the range over which peripheral objects can be seen when one gazes on a single point. More specifically, the face is held stationary relative to the perimeter, and the test subject is asked to stare at a central mark displayed at a display area within the perimeter. While in this state, lights or the like are made to appear at the periphery of the display area, and the test subject is asked to sound a buzzer when he or she sees these lights. By investigating the locations at which the test subject can or cannot see lights in this fashion, the visual field, and gaps therein, are investigated (see http://medical-checkup.info/article/43671142.html and http://www.nichigan.or.jp/public/disease/ryokunai_ryokunai.jsp).

PRIOR ART REFERENCES

Patent References

Patent Reference No. 1: Japanese Patent Application Publication Kokai No. H07[1995]-313457
Patent Reference No. 2: WO2003/057021

SUMMARY OF INVENTION

Problem to be Solved by Invention

However, while the aforementioned minimum separable acuity should in principle be consistent with retinal resolution, it was found as a result of experimentation by the present inventor(s) that minimum separable acuity as measured using Landolt rings is not consistent with retinal resolution. That is, although Landolt rings are an internationally recognized standardized test symbol, it was found that in reality they do not possess sufficient precision for testing of minimum separable acuity.

Moreover, attempts have been made in recent years to use information communication equipment to automate measurement of visual acuity. Where such automatic measurement has been carried out, a liquid crystal display or other such display apparatus has been used. However, because such Landolt rings have portions formed from curves, there has been the problem that as the standardized test symbol is made increasingly small, it becomes increasingly difficult to accurately render the Landolt ring using a liquid crystal display.

On the other hand, studies have also been performed on standardized test symbols that can be used in place of Landolt rings and that are suitable for automatic measurement (see Patent Reference Nos. 1 and 2). While such standardized symbols do tend to retain their shapes when displayed at a liquid crystal display or the like better than would be the case with a Landolt ring, there have been no studies with respect to Patent Reference Nos. 1 and 2 to determine whether or not the minimum separable acuity obtained as a result of testing is consistent with retinal resolution.

Furthermore, with regard to testing of visual field as well, conventional tests have been such that on the order of 30 minutes has been required to complete testing of both eyes, and since the gaze is held stationary during testing, the burden on the test subject during testing is large. And there has also been occurrence of problems such as the fact that because testing takes a long time, ability to concentrate diminishes as testing proceeds, resulting in lapses in ability to perceive light even when there is no defect. In addition, there has also been the problem that to properly carry out testing of visual field, it has been necessary for a technician who administers the test to operate the apparatus and to monitor for test errors, and thus a large burden is placed not only on the test subject but also on the test technician.

The present invention was conceived in light of such situation, it being an object thereof to provide a visual field measuring method and a visual field measuring apparatus that will make it possible to reduce the burden on the test subject and the test technician.

Furthermore, it is also an object thereof to provide an optotype suitable for the visual field measuring apparatus and the visual field measuring method of the present invention as well as for automated measurement and permitting the minimum separable acuity obtained as a result of testing to be made consistent with retinal resolution.

Means for Solving Problem

Visual Field Measuring Method

A visual field measuring method in accordance with a first aspect of the present invention is a method in which standardized test symbols are sequentially displayed at a display to measure visual field, characterized in that it comprises a reference standardized symbol display operation in which a standardized test symbol is displayed at a reference location provided at a center of the display; a reference input operation in which a test subject is made to input the fact that the standardized test symbol displayed at said reference standardized symbol display operation has been recognized; a peripheral standardized symbol display operation in which, following the input of the fact that the standardized test symbol was recognized at said reference input operation, a standardized test symbol is displayed at a peripheral location which is different from the reference location; and a peripheral input operation in which the test subject is made to input the fact that the standardized test symbol displayed at said peripheral standardized symbol display operation has been recognized; wherein from the reference standardized symbol display operation to the peripheral input operation is executed in repeated and sequential fashion, and a response time from when the standardized test symbol is displayed at the peripheral standardized symbol display operation to when the input is performed by the test subject at the peripheral input operation is measured.

A visual field measuring method in accordance with a second aspect of the present invention, in the context of the first aspect of the present invention, is characterized in that the standardized test symbol displayed at the reference standardized symbol display operation is a standardized test symbol for testing visual acuity; and the test subject is made to input an orientation of the standardized test symbol at the reference standardized symbol display operation.

A visual field measuring method in accordance with a third aspect of the present invention, in the context of the first or second aspect of the present invention, is characterized in that the standardized test symbol displayed at the peripheral standardized symbol display operation is a standardized test symbol for testing visual acuity; the test subject is made to input an orientation of the standardized test symbol at the peripheral standardized symbol display operation; and when a fractional number of times that the orientation input by the test subject at the peripheral input operation does not match the orientation of the standardized test symbol displayed at the peripheral standardized symbol display operation is greater than or equal to a prescribed value, or when the orientation input by the test subject at the peripheral input operation matches the orientation of the standardized test symbol displayed at the peripheral standardized symbol display operation but the response time is greater than or equal to a prescribed time, said peripheral location is determined to be a scotoma.

A visual field measuring method in accordance with a fourth aspect of the present invention, in the context of the third aspect of the present invention, is characterized in that a criterion for the determination as to whether the scotoma is present is a best-fit line obtained by performing linear approximation on a graph plotting the response time in such fashion that offset information pertaining to the standardized test symbol displayed at the peripheral standardized symbol display operation is plotted on a horizontal axis and the response time is plotted on a vertical axis.

A visual field measuring method in accordance with a fifth aspect of the present invention, in the context of the fourth aspect of the present invention, is characterized in that data from which scotoma candidates have been removed is employed for the best-fit line; a scotoma dividing line which is parallel to the best-fit line is extracted based on the scotoma candidates; and a location which is within the scotoma candidates and for which the response time is greater than that indicated by the scotoma dividing line is determined to be a scotoma.

A visual field measuring method in accordance with a sixth aspect of the present invention, in the context of the fifth aspect of the present invention, is characterized in that data for a portion of the scotoma candidates that are located in the Marriotte blind spot is employed to extract a scotoma determination line.

A visual field measuring method in accordance with a seventh aspect of the present invention, in the context of any of the first through sixth aspects of the present invention, is characterized in that standardized test symbols of differing size are displayed at the reference location to test visual acuity, and response time from when the standardized test symbol is displayed until when a direction of the standardized test symbol is input by the test subject is measured; and a size of the standardized test symbol to be used to test visual field is determined based on a relationship between the sizes of the standardized test symbols and the response times.

A visual field measuring method in accordance with an eighth aspect of the present invention, in the context of any of the first through seventh aspects of the present invention, is characterized in that the standardized test symbol is an ARO.

Visual Field Measuring Apparatus

A visual field measuring apparatus in accordance with a ninth aspect of the present invention is characterized in that it comprises a display that displays a standardized test symbol; an input unit that accepts input from a test subject of the fact that the standardized test symbol displayed by said display has been recognized; and a display controller that controls timing and location at which the standardized test symbol is displayed by the display; wherein said display controller comprises reference standardized symbol display functionality that causes a standardized test symbol to be displayed at a reference location at the display; peripheral standardized symbol display functionality that causes a standardized test symbol to be displayed at a peripheral location which is different from the reference location at the display; display switching functionality that performs switching between the reference standardized symbol display functionality and the peripheral standardized symbol display functionality based on a signal from the input unit; and response time measuring functionality that measures a time from when the peripheral standardized symbol display functionality causes the standardized test symbol to be displayed until when the test subject enters the input at the input unit.

A visual field measuring apparatus in accordance with a tenth aspect of the present invention, in the context of the ninth aspect of the present invention, is characterized in that the standardized test symbol displayed at the reference location of the display by the reference standardized symbol display functionality is a standardized test symbol for testing visual acuity; and the input unit is constituted so as to accept input of an orientation of the standardized test symbol by the test subject who recognizes the standardized test symbol displayed at the reference location of the display by the reference standardized symbol display functionality.

A visual field measuring apparatus in accordance with an eleventh aspect of the present invention, in the context of the ninth or tenth aspect of the present invention, is characterized in that the standardized test symbol displayed at the peripheral location of the display by the peripheral standardized symbol display functionality is a standardized test symbol for testing visual acuity; the input unit is constituted so as to accept input of an orientation of the standardized test symbol by the test subject who recognizes the standardized test symbol displayed at the peripheral location of the display by the peripheral standardized symbol display functionality; the display controller has scotoma determining functionality for making a determination as to whether a scotoma is present based on the input which is entered at the input unit; and said scotoma determining functionality has scotoma determining functionality such that when a fractional number of times that the orientation input at the input unit when the standardized test symbol is displayed at the peripheral location does not match the orientation of the standardized test symbol displayed by means of the peripheral standardized symbol display functionality displayed by the peripheral standardized symbol display functionality is greater than or equal to a prescribed value, or when the orientation input at the input unit when the standardized test symbol is displayed at the peripheral location matches the orientation of the standardized test symbol displayed by the peripheral standardized symbol display functionality but a measured time measured by the response time measuring functionality is greater than or equal to a prescribed time, the peripheral location is determined to be a scotoma.

A visual field measuring apparatus in accordance with a twelfth aspect of the present invention, in the context of the eleventh aspect of the present invention, is characterized in that the scotoma determining functionality has functionality such that a criterion for the determination as to whether the scotoma is present is a best-fit line obtained by performing linear approximation on a graph plotting the measured response time in such fashion that offset information pertaining to the standardized test symbol displayed by the peripheral standardized symbol display functionality is plotted on a horizontal axis and the response time is plotted on a vertical axis.

A visual field measuring apparatus in accordance with a thirteenth aspect of the present invention, in the context of the twelfth aspect of the present invention, is characterized in that the scotoma determining functionality has functionality such that data from which scotoma candidates have been removed is employed for the best-fit line; a scotoma dividing line which is parallel to the best-fit line is extracted based on the scotoma candidates; and a location which is within the scotoma candidates and for which the response time is greater than that indicated by the scotoma dividing line is determined to be a scotoma.

A visual field measuring apparatus in accordance with a fourteenth aspect of the present invention, in the context of the thirteenth aspect of the present invention, is characterized in that the scotoma determining functionality has functionality such that data for a portion of the scotoma candidates that are located in the Marriotte blind spot is employed to extract a scotoma determination line.

A visual field measuring apparatus in accordance with a fifteenth aspect of the present invention, in the context of any of the ninth through fourteenth aspects of the present invention, is characterized in that the display controller is equipped with standardized symbol size determining functionality for determining sizes of the standardized test symbols displayed at the reference location and the peripheral location; and said standardized symbol size determining functionality has response time measuring functionality for causing standardized test symbols of differing size to be displayed at the reference location to test visual acuity, and measuring response times from when said standardized test symbols are displayed until when directions of said standardized test symbols are input by the test subject; and size determining functionality for causing a size of the standardized test symbol that will be used to test visual field to be determined based on a relationship between the sizes of the standardized test symbols and the response times measured by said response time measuring functionality.

A visual field measuring apparatus in accordance with a sixteenth aspect of the present invention, in the context of any of the ninth through fifteenth aspects of the present invention, is characterized in that the standardized test symbol is an ARO.

Optotype

An optotype in accordance with a seventeenth aspect of the present invention is a standardized test symbol used to test minimum separable acuity, characterized in that it is formed from a pair of parallel lines provided in mutually parallel fashion, and a single connecting line that connects mutually opposed end edges of the lines making up said pair of parallel lines; wherein the pair of parallel lines are formed so as to be of the same length; wherein the connecting line is provided in such fashion as to be perpendicular to the pair of parallel lines; and wherein widths of the lines making up the pair of parallel lines, width of a gap between the pair of parallel lines, and width of the connecting line are formed so as to all be the same length.

An optotype in accordance with an eighteenth aspect of the present invention, in the context of the seventeenth aspect of the present invention, is characterized in that the standardized test symbol is formed in such fashion that lengths of the lines making up the pair of parallel lines, and distance between outer edges of the pair of parallel lines, are the same length.

An optotype in accordance with a nineteenth aspect of the present invention, in the context of the seventeenth or eighteenth aspect of the present invention, is characterized in that a ratio between lengths and widths of the lines making up the pair of parallel lines is chosen so as to be 2:1 to 5:1.

Benefit of the Invention

Visual Field Measuring Method

The first aspect of the present invention makes it possible to accurately measure scotomas and the Marriotte blind spot with a test that is easy and takes a small amount of time. This being the case, it is able to contribute to early discovery of any of a variety of diseases including glaucoma, pigmentary degeneration of the retina, diabetic retinopathy, detachment of the retina, and macular degeneration; as well as to evaluation and confirmation of the degree to which any of the various respective diseases has progressed.

Because it makes it possible to definitively cause the gaze of the test subject to be directed toward a reference location, the second aspect of the present invention makes it possible to increase test precision.

Because it makes it possible to reduce occurrence of misdeterminations in which scotomas are determined to be normal areas, the third aspect of the present invention makes it possible to detect scotomas with good precision.

Because it makes it possible to compensate for differences in response time depending on the location(s) at which standardized test symbol(s) are displayed, the fourth aspect of the present invention makes it possible to more accurately determine whether scotoma(s) are present.

Because scotoma candidate data is used to create a scotoma determination line, the fifth aspect of the present invention makes it possible to increase the precision with which locations are determined to be scotomas.

Because data for the Marriotte blind spot, which is definitely a scotoma, is used to create a scotoma determination line, the sixth aspect of the present invention makes it possible to increase the precision with which locations are determined to be scotomas.

Because it makes it possible to make the size of the standardized test symbol that will be used to test visual field be an appropriate size, the seventh aspect of the present invention makes it possible to stabilize response time. Accordingly, it will be possible to improve test precision when carrying out visual field testing using standardized test symbols.

Because it makes it possible to cause recognition of standardized test symbol(s) by a test subject to be commensurate with the condition of the actual visual acuity of the test subject, the eighth aspect of the present invention makes it possible to increase test precision.

Visual Field Measuring Apparatus

The ninth aspect of the present invention makes it possible to accurately measure scotomas and the Marriotte blind spot with a test that is easy and takes a small amount of time. This being the case, it is able to contribute to early discovery of any of a variety of diseases including glaucoma, pigmentary degeneration of the retina, diabetic retinopathy, detachment of the retina, and macular degeneration; as well as to evaluation and confirmation of the degree to which any of the various respective diseases has progressed.

Because it makes it possible to definitively cause the gaze of the test subject to be directed toward a reference location, the tenth aspect of the present invention makes it possible to increase test precision.

Because it makes it possible to reduce occurrence of misdeterminations in which scotomas are determined to be normal areas, the eleventh aspect of the present invention makes it possible to detect scotomas with good precision.

Because it makes it possible to compensate for differences in response time depending on the location(s) at which standardized test symbol(s) are displayed, the twelfth aspect of the present invention makes it possible to more accurately determine whether scotoma(s) are present.

Because scotoma candidate data is used to create a scotoma determination line, the thirteenth aspect of the present invention makes it possible to increase the precision with which locations are determined to be scotomas.

Because data for the Marriotte blind spot, which is definitely a scotoma, is used to create a scotoma determination line, the fourteenth aspect of the present invention makes it possible to increase the precision with which locations are determined to be scotomas.

Because it makes it possible to make the size of the standardized test symbol that will be used to test visual field be an appropriate size, the fifteenth aspect of the present invention makes it possible to stabilize response time. Accordingly, it will be possible to improve test precision when carrying out visual field testing using standardized test symbols.

Because it makes it possible to cause recognition of standardized test symbol(s) by a test subject to be commensurate with the condition of the actual visual acuity of the test subject, the sixteenth aspect of the present invention makes it possible to increase test precision. And because the standardized test symbol(s) do not have curved portion(s), since it will be possible to decrease the time spent waiting for standardized test symbol(s) to be displayed, it will be possible to reduce test time. Moreover, because there is no occurrence of incidents in which testing is skipped due to display error or the like, it will be possible to automate testing of visual field.

Optotype

The seventeenth through nineteenth aspects of the present invention permit attainment of a minimum separable acuity that is consistent with retinal resolution. And because they do not have curved portion(s), it will be possible when causing the standardized test symbol(s) to be displayed in digital fashion for these to be displayed quickly and accurately. Accordingly, it will be possible to automate testing of visual acuity.

BRIEF DESCRIPTION OF THE DRAWINGS

FIG. 5 Map of locations for carrying out measurement of scotomas.

EMBODIMENTS FOR CARRYING OUT THE INVENTION

The visual field measuring method of the present invention, which is a method for testing the visual field of a test subject and for detecting gaps and so forth therein, possesses the characteristic that it makes it possible for testing to be carried out in simple fashion.

The visual field measuring apparatus of the present invention, which is an apparatus for use in testing the visual field of a test subject, possesses the characteristic that it makes it possible for testing to be carried out in simple fashion.

The optotype of the present invention, which is a standardized test symbol for use in testing minimum separable acuity, possesses the characteristic that it is shaped so as to permit attainment of a minimum separable acuity that is more consistent with retinal resolution than Landolt rings and other such conventional standardized test symbols.

Note that the optotype of the present invention is suited not only for testing of minimum separable acuity but also for use as a standardized test symbol when testing a person's visual field. More specifically, it may be used as a standardized test symbol in the visual field measuring method of the present invention to determine location(s) at which a person has scotoma(s) and/or whether scotoma(s) are present.

Optotype

Description will first be given with respect to an optotype (hereinafter "Accurate Resolution Optotype (ARO)") capable of being used with the visual field measuring apparatus and the visual field measuring method of the present invention. The optotype of the present invention is the ARO that is referred to in the claims.

Figure 2:
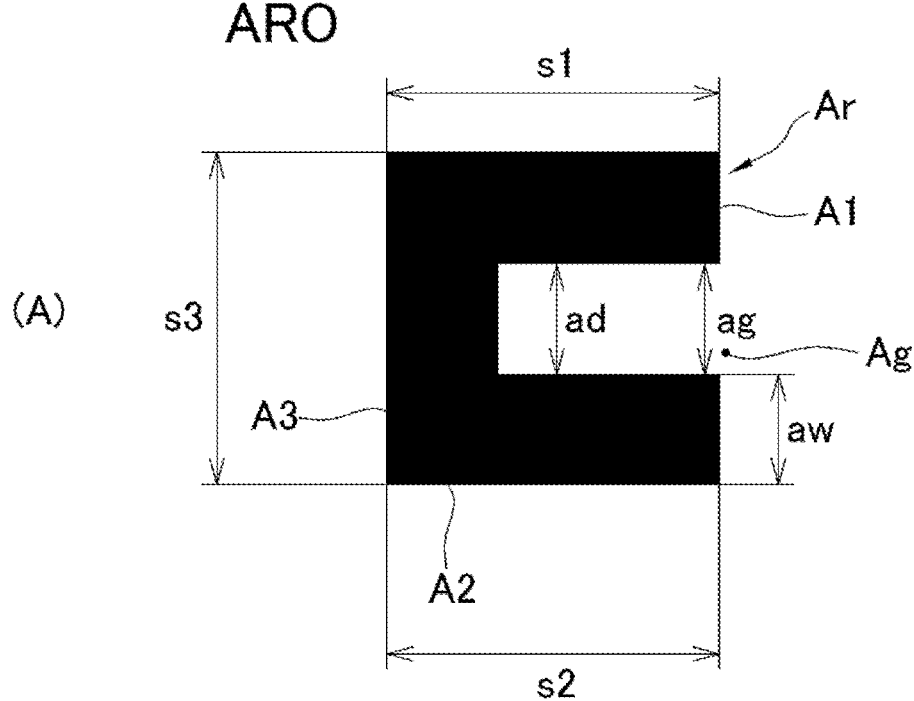
FIG. 2 (A) is a schematic explanatory diagram of an Accurate Resolution Optotype (ARO), which is an optotype in accordance with the present invention; (B) is a schematic explanatory diagram of Landolt ring L.
Figure 2:
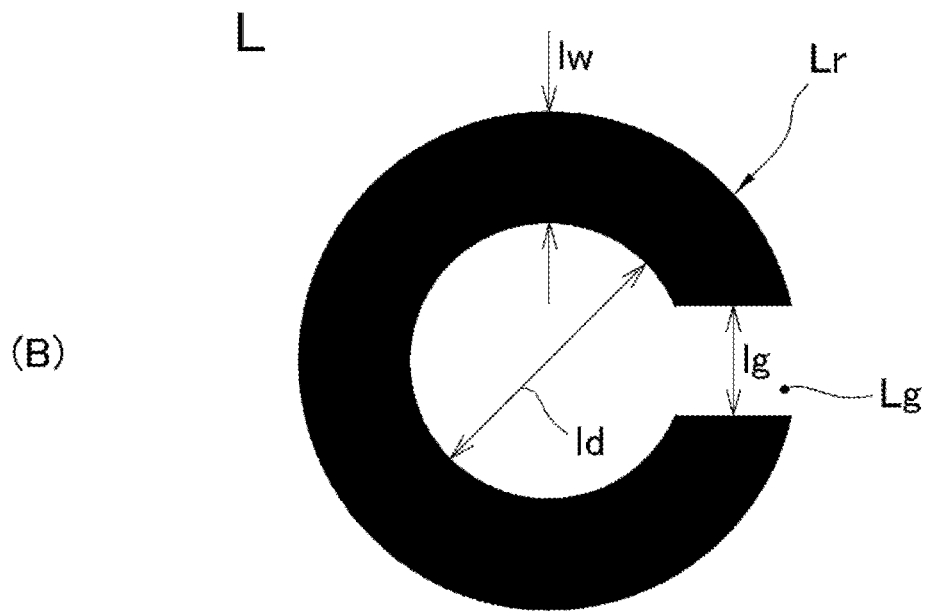

FIG. 2 (A) shows an ARO. This ARO is such that notch Ag is formed at a portion of ring-like line Ar (i.e., made up of lines A1 to A3) in similar fashion as Landolt ring L (FIG. 2 (B)) which is used to carry out conventional testing of visual acuity (i.e., testing of minimum separable acuity).

However, at Landolt ring L, ring-like line Lr is circular, and the portion enclosed by this ring-like line Lr is likewise circular. On the other hand, at the ARO, ring-like line Ar (formed from lines A1 to A3) is rectangular, and the portion enclosed by this line Ar is likewise rectangular. In addition, at the ARO, unlike Landolt ring L, ring-like line Ar being formed from only linear segments, it has no portion that is curved.

In addition, at Landolt ring L, width lg of notch Lg and diameter ld of the portion enclosed by line Lr are completely different. On the other hand, the ARO is of such shape as to cause width ag of notch Ag and width ad of the rectangular portion enclosed by line Ar to be the same width.

Moreover, at Landolt ring L, while line width lw and width lg of notch Lg are of the same width, the notch is not rectangular in shape. On the other hand, at the ARO, this is rectangular, being shaped so as to cause width ag of notch Ag to be of the same width as line width aw of ring-like line Ar (i.e., respective lines A1 through A3).

Because the ARO possesses aspects such as those mentioned above that are consistent with Landolt ring L, it is possible by varying the size and/or location of notch Ag thereof to use it for testing of visual acuity in similar fashion as Landolt ring L. That is, by having a person say where notch Ag of the ARO is, it is possible to test whether the person has visual acuity sufficient to recognize width ag of notch Ag of the ARO.

On the other hand, because the ARO possesses aspects such as those mentioned above that are different from Landolt ring L, it allows visual acuity to be tested more accurately than is the case with Landolt ring L. That is, using an ARO to carry out testing of visual acuity will permit attainment of test results that are such that the minimum separable acuity detected as a result of testing of visual acuity is consistent with retinal resolution.

The reason for this is as follows.

First, where a striped pattern is used to measure the minimum stripe width that can be recognized as a striped pattern, that minimum stripe width will more or less agree with retinal resolution. If the spatial frequency spectrum of this striped pattern is analyzed, it is possible to obtain the peak spatial frequency. The spatial frequency corresponding to this peak (peak frequency) is the spatial frequency that is most easily perceived by the test subject, which is to say that it is the minimum stripe width that is recognizable by the test subject which is detected when the striped pattern is used.

The ARO and Landolt ring L test visual acuity based on whether or not a notch can be recognized. This being the case, it is possible to understand the ARO and Landolt ring L to be testing visual acuity based on whether the notch can be recognized as a stripe. Accordingly, if the peak frequency of the spatial frequency spectrum of the ARO or Landolt ring L is the same as the peak frequency of the spatial frequency spectrum of the striped pattern for which the line width is the same as the width of the notch in the ARO or Landolt ring L, it is thought that the results of testing of visual acuity using the ARO or Landolt ring L will agree with the minimum stripe width measured using the striped pattern. In other words, it is thought that the results (minimum separable acuity) of testing of visual acuity using the ARO or Landolt ring L can be made consistent with retinal resolution.

When the spatial frequency spectrum of Landolt ring L is analyzed, it is found to have a peak at a spatial frequency that is lower than the spatial frequency that might otherwise have been expected to be discerned (i.e., the frequency of the notch), there being no peak at the peak frequency of the striped pattern of the same line width. That is, while it is possible when carrying out testing of visual acuity using Landolt ring L that a test subject may be able to recognize widths narrower than the retinal resolution, it is thought that it may be the case that proper testing of the retinal resolution of the test subject may not be possible.

On the other hand, when the spatial frequency spectrum of the ARO is analyzed, it is found to have a peak at the spatial frequency where one might have expected one to be discerned (i.e., the frequency of the notch), there being a peak at the peak frequency of the striped pattern of the same line width. In other words, when testing visual acuity using the ARO, it is thought that proper testing of the retinal resolution of the test subject will be possible In addition, because the ARO does not have a curved portion, it will be possible when causing this to be displayed at a display apparatus to cause it to be displayed quickly and accurately. For example, where this is displayed in dot matrix fashion, it is sufficient merely by specifying the locations to be displayed (i.e., the cells or the like to be displayed) to cause display of the ARO. For example, an ARO might be displayed in such fashion that the number of pixels is 3 pixel×3 pixel while yet causing this to be displayed such that the shape thereof is clear. This being the case, it will be possible to carry out testing of visual acuity using the ARO through use of a smartphone, tablet terminal, or the like. That is, it will be possible even for individuals to easily carry out testing of visual acuity. Furthermore, by causing ARO(s) to be displayed as appropriate and making it possible to accept input of the results thereof, it will also be possible to automate testing of visual acuity.

Moreover, the ARO may be used as standardized symbol not only for testing of visual acuity, it being possible, by incorporating it into testing of other aspects of visual performance such as testing of visual field (described below), to increase the precision of any of a variety of tests.

Shape of the ARO will now be described in more detail.

As shown at FIG. 2, an ARO comprises a pair of parallel lines A1, A2 which are provided in mutually parallel fashion. The lines making up this pair of parallel lines A1, A2 are formed so as to be of the same length, and the mutually opposed end edges (the end portions at the left side in FIG. 2 (A)) thereof are connected by connecting line A3. This connecting line A3 is provided in such fashion as to be perpendicular to pair of parallel lines A1, A2. That is, the ARO is formed so as to be in the shape of the katakana character ko (or stating this in terms of an alphabetic character, in the shape of a squarish U). What is more, the ARO is formed so as to cause the widths of the lines making up the pair of parallel lines A1, A2, the width of the gap between the pair of parallel lines A1, A2 (i.e., the width of notch Ag), and the width of the line at connecting line A3, to all be the same length. Because it is formed so as to be of such shape, the ARO makes it possible to attain benefits such as are described above.

The ARO is formed so as to cause lengths s1, s2 of the lines making up the pair of parallel lines A1, A2, and distance s3 between the outer edges of the pair of parallel lines A1, A2, to be the same length. This is so as to cause the ARO to be in the shape of a square. It is necessary during testing of visual acuity that it not be possible to guess at the location of the notch based on the external shape of the standardized symbol. Causing the ARO to be in the shape of a square makes it impossible to guess at the direction of the notch by rotating the external shape. That is, causing the ARO to be in the shape of a square makes it possible to carry out accurate testing of visual acuity.

Visual Field Testing

Use of an optotype (ARO) as described above will make it possible, through use of a test apparatus as described below, to quickly and easily carry out testing of visual field, or in more specific terms, testing to determine whether or not scotoma(s) are present within the visual field. For example, with the visual field test apparatus that has been employed conventionally, it being necessary to hold stationary and prevent movement of the gaze at the time of testing, it has been necessary to hold the face of the test subject stationary and for the gaze to be held stationary. In addition, to remove the influence of external light, it has been necessary at the time of testing to carry out testing in such state that the entire front side of the face of the test subject is covered. Moreover, to properly carry out testing, it has been necessary for a technician who administers the test to operate the apparatus and to monitor for test errors. However, with a test apparatus in accordance with the present embodiment using an optotype as described above, there is no need to constrain the face or the like of the test subject, and it is not necessary consider the influence of external light. This being the case, because it becomes unnecessary to employ fixtures or the like with which to cover the face of the test subject, benefits can be obtained such as the fact that the apparatus can be simplified and the fact that testing can be carried out without the need for a specialized apparatus. In addition, because test precision can be maintained even when measurement is carried out by the test subject alone, it permits attainment of the benefit by which not only the burden on the test subject but also the burden on the test technician can be reduced.

In addition, because testing is made possible through use of a simple method and apparatus, it contributes to early discovery of any disease that the test subject may have. For example, based on the situation with respect to scotoma(s) as obtained from the results of testing of visual field, early discovery of diseases such as glaucoma, pigmentary degeneration of the retina, diabetic retinopathy, detachment of the retina, and macular degeneration is made possible.

Visual Field Test Apparatus 1

Visual field test apparatus 1 which uses an optotype as described above is described below.

Figure 1:
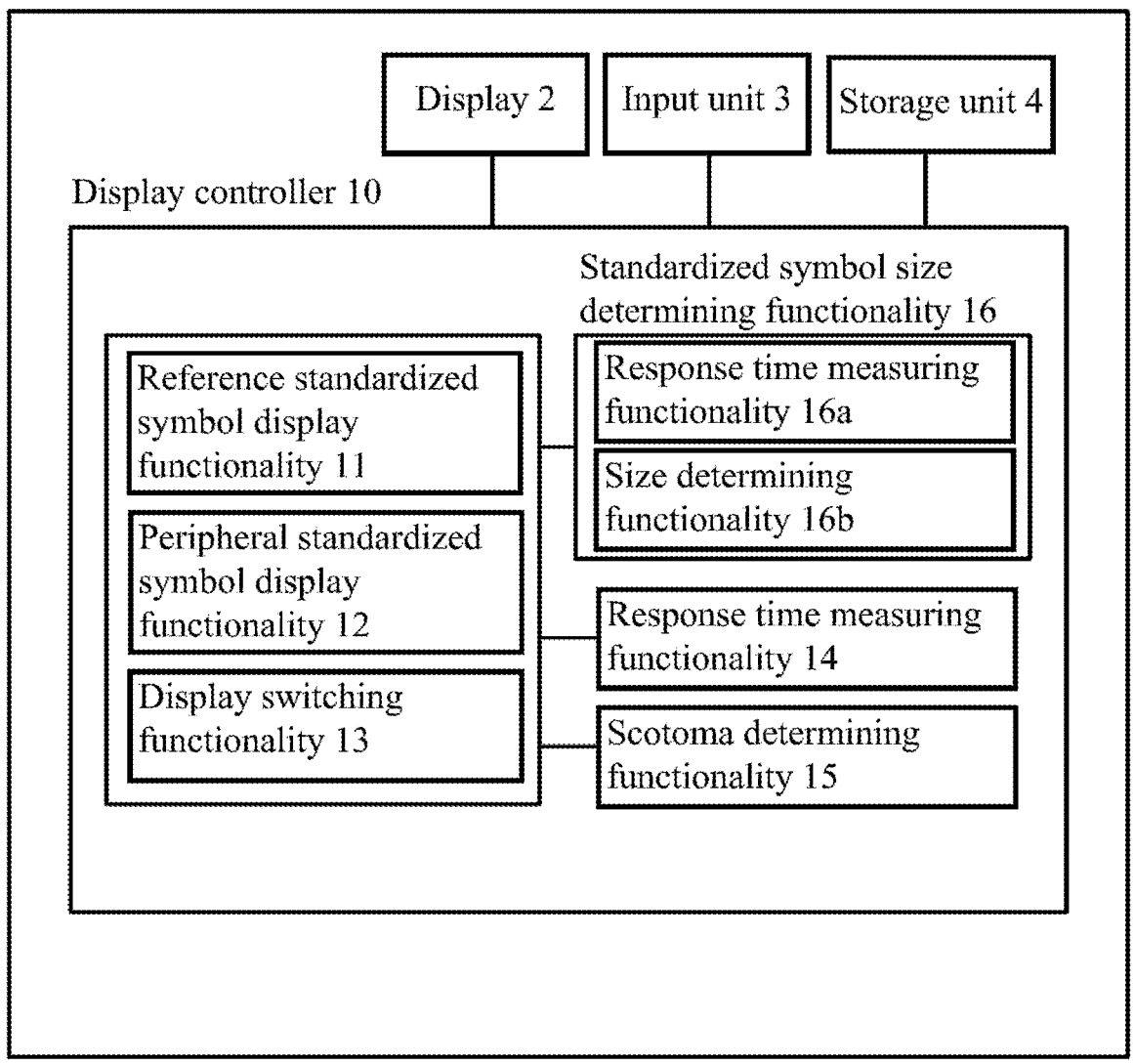
FIG. 1 Block diagram of visual field measuring apparatus 1 in accordance with the present embodiment.

As shown in FIG. 1, visual field test apparatus 1 is provided with display 2, input unit 3, storage unit 4, and display controller 10. At this visual field test apparatus 1, the location at which display controller 10 causes an ARO (standardized test symbol) to be displayed on display 2 is variable. In addition, a constitution is employed in which input is accepted at input unit 3 of the location of notch Ag of the ARO that is displayed (i.e., the orientation of the ARO).

Standardized Test Symbol

Note that the standardized test symbols displayed by visual field test apparatus 1 are not limited to AROs, it being possible to employ other standardized test symbol(s). For example, it is possible to employ Landolt rings, characters from the native language of the test subject, and/or the like. However, if an ARO is used as standardized test symbol, because it will be possible to cause recognition of the standardized test symbol by the test subject to be commensurate with the condition of the actual visual acuity of the test subject, it will be possible to increase test precision.

What is more, because the ARO does not have a curved portion, it will be possible to cause it to be displayed by display 2 in accurate and high-speed fashion. Accordingly, because it will be possible to decrease the time spent waiting for the standardized test symbol to be displayed, it will be possible to reduce test time. Moreover, because there is no occurrence of incidents in which testing is skipped due to display error or the like, it is possible to automate testing of visual field using visual field test apparatus 1.

Figure 4:
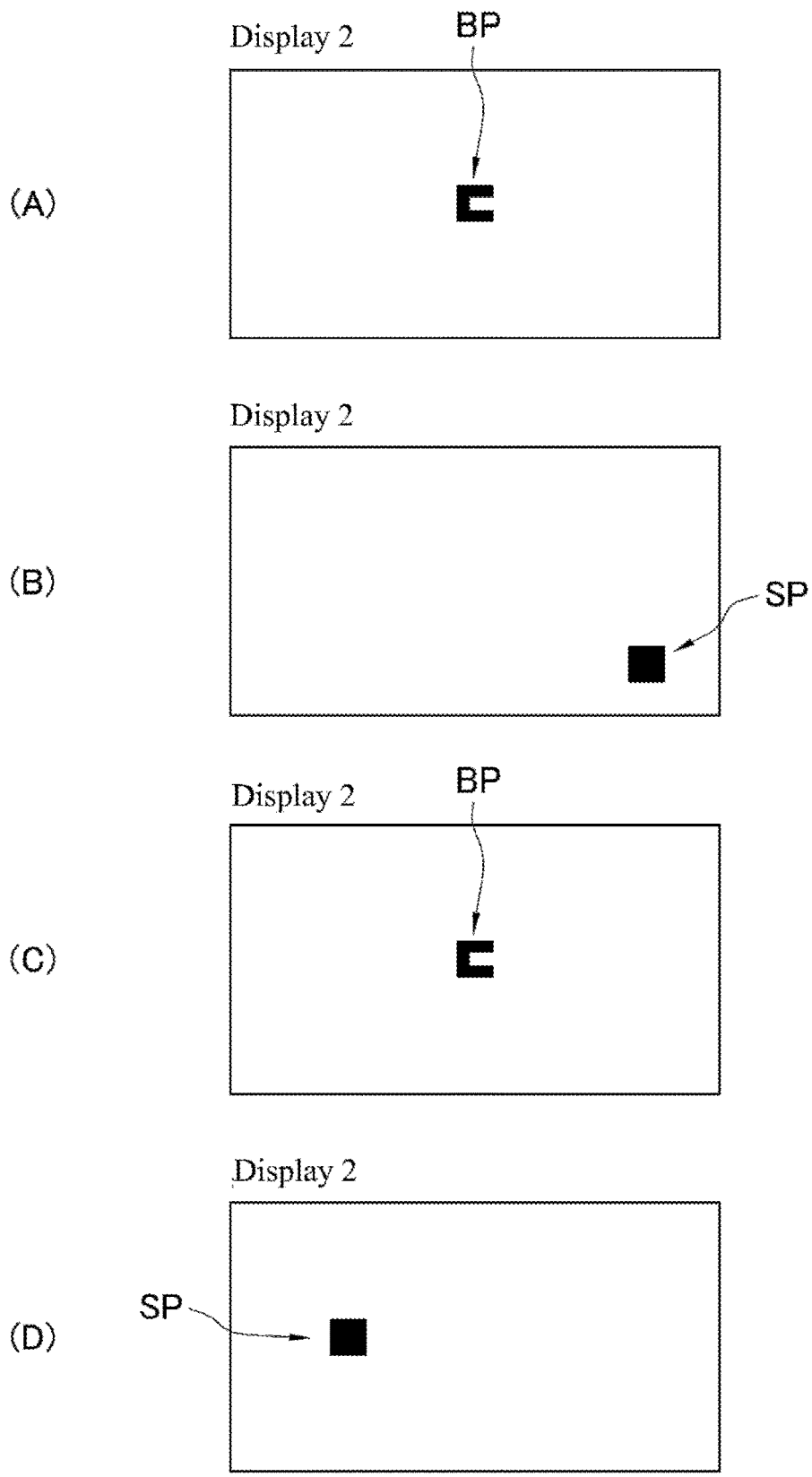
FIG. 4 Schematic diagram for explaining a situation in which standardized symbols displayed at peripheral locations SP might be varied in the context of a visual field measuring method using visual field measuring apparatus 1 in accordance with the present embodiment.

Note that it is not necessary that the standardized symbols displayed at reference location BP and at peripheral location SP be the same type of standardized symbol. That is, the standardized symbols displayed at reference location BP and at peripheral location SP may be of different types. For example, ARO(s) might be displayed at reference location BP, and character(s) or the like might be displayed at peripheral location SP. In particular, with respect to the standardized symbol(s) displayed at peripheral location(s) SP, because it is sufficient so long as the test subject is able to recognize that a standardized symbol has been displayed, this may be a simple black dot or the like (see FIG. 4). In such case, with respect to input unit 3, described below, this will be sufficient so long as it is able to accept input from the test subject of the fact that a standardized symbol has been recognized at peripheral location SP. For example, where input unit 3 is a keyboard or the like, this may be such as to recognize that proper input has been made not when some particular key is depressed but when any key has been depressed. On the other hand, with respect to the standardized symbol that is displayed at reference location BP, so as to definitively cause the gaze of the test subject to be directed toward reference location BP, it is preferred that an ARO or other such standardized test symbol be employed thereat. That is, with respect to the standardized symbol that is displayed at reference location BP, it is preferred that a standardized symbol be employed that cannot be recognized unless the test subject directs his or her gaze at, and looks at, the standardized symbol.

Note that the description which follows is given in terms of an example in which AROs are displayed at both reference location(s) BP and peripheral location(s) SP.

Display 2

Display 2 is capable of causing information supplied from the exterior and/or display controller 10 to be displayed based on instructions from the exterior and/or display controller 10. More specifically, it is capable of causing ARO(s) to be displayed at prescribed location(s) (reference location(s) BP and/or peripheral location(s) SP, described below) based on instruction(s) from display controller 10.

Note that where display 2 is such as to be able to cause display of ARO(s) with a certain degree of speed, any sort of display apparatus might be employed thereas. For example, it is possible to employ liquid crystal display(s), plasma display(s), and/or other such known display apparatus(es). While there is no particular limitation with regard to the size of this display 2, one which is as small as possible is preferred, because this will allow the apparatus to be made compact. The visual field over which a person can recognize characters and the like is a range that is within only on the order of about 30 degrees from the center of the visual field. Accordingly, e.g., where the viewing distance (distance from the test subject to display 2) is 450 mm, it will be sufficient to allow testing of visual field to be carried out if the size of display 2 is such that the lengths in the vertical and horizontal directions are on the order of 300 mm×520 mm (23-inch display). Note that there is no particular limitation with regard to the shape of display 2, it being possible for this to be square or rectangular or any other shape.

Note that it is possible to use a head-mounted display, provided at the interior of which there may be a liquid crystal or other such screen, as display 2. Where a head-mounted display is employed, this will facilitate maintenance of a constant distance from the eye of the person to the screen. Furthermore, in the event that the person moves his or her face, because this will cause the screen to move in accompaniment to the movement of the face, it will be possible to eliminate the influence of facial motion. Moreover, if displays for the right eye and for the left eye are respectively provided, it will be possible to create a situation such that each eye is prevented from seeing the screen for the other eye. Doing this will make it possible to easily carry out testing involving both eyes and testing involving only one eye. In addition, by causing the left and right eyes to be randomly subjected to testing so as to prevent the test subject from recognizing which eye is being tested, because this will make it possible to prevent the test subject from deliberately manipulating the test results, it will permit increase in test precision. Note that where a situation is created such that each eye is prevented from seeing the screen for the other eye, when carrying out testing of both eyes, the images displayed at the respective screens are adjusted to prevent the person from experiencing discomfort when the images that are displayed on the respective screens for the right eye and the left eye are viewed by the respective eyes.

Input Unit 3

Input unit 3 is for accepting input by the test subject of the orientation(s) of ARO(s) displayed at display 2. This input unit 3 is capable of accepting input by the test subject of the orientation of the ARO; more specifically, the location i.e., which among four directions, these being top, bottom, left, or right at which notch Ag of the ARO is arranged. For example, a keyboard, joy stick, mouse, or other such input device might be employed as input unit 3. Use of the cursor keys on a keyboard is preferred, since this will make it possible to lessen the influence of proficiency in operating the input device. Furthermore, with regard to use of a joy stick as well, because all that will be required is to move the joy stick in the direction of notch Ag (front and back corresponding to top and bottom), this will make it possible to lessen the influence of proficiency in operating the input device.

This input unit 3 also has functionality such that when input has been made thereto from the test subject, a signal providing notification of the fact that such input has occurred is sent to display controller 10 (more specifically, to the respective functionalities of display controller 10).

Storage Unit 4

Storage unit 4, which is connected to display controller 10, has functionality for storing information sent thereto from the respective functionalities of display controller 10. For example, it might have functionality for causing information pertaining to the ARO that has been displayed and the location at which the ARO has been displayed which is sent thereto from peripheral standardized symbol display functionality 12 of display controller 10, the direction which was input at input unit 3, and the response time (described below), to be stored in associated fashion.

In addition, storage unit 4 has functionality for causing information stored thereat to be sent to the exterior or supplied to display 2 based on instructions from the exterior or display controller 10.

Display Controller 10

Display controller 10 has functionality for controlling the timing with which and the location(s) at which ARO(s) are displayed at display 2. That is, display controller 10 controls display of ARO(s) based on signal(s) from input unit 3. This display controller 10 is provided with reference standardized symbol display functionality 11, peripheral standardized symbol display functionality 12, display switching functionality 13, response time measuring functionality 14, and scotoma determining functionality 15.

Reference Standardized Symbol Display Functionality 11

Reference standardized symbol display functionality 11 has functionality for causing ARO(s) to be displayed at reference location(s) BP of display 2. More specifically, reference standardized symbol display functionality 11 has functionality such that when a command is sent thereto from display switching functionality 13, information (reference display information) including information pertaining to the location of reference location BP and information pertaining to the ARO to be displayed at reference location BP is sent to display 2, causing display of the ARO at display 2.

The information pertaining to the location of the reference location BP is information such as the coordinates of the reference location BP at display 2. Reference location BP, which is a preestablished location, is chosen to be an appropriate location in light of the size and shape of display 2. For example, reference location BP might be chosen so as to be in the center of display 2. Note that reference location BP may be chosen so as to be at a location that is somewhat offset from the center of display 2.

The information pertaining to the ARO to be displayed at reference location BP is information pertaining to the orientation of the ARO and/or the size of ARO to be displayed. The size of the ARO to be displayed by reference standardized symbol display functionality 11 may be a predefined size or it may be varied so as to be of appropriate size in correspondence to the test subject. For example, AROs might be used to measure the visual acuity of the test subject, and an ARO which is somewhat larger (e.g., one step larger) than the ARO found to be the limit of the visual acuity might be employed. Furthermore, orientation of the ARO which is caused to be displayed by reference standardized symbol display functionality 11 might be varied in random fashion, or it might be made to always be of the same orientation.

Furthermore, the timing with which ARO(s) are caused to be displayed at reference location BP by reference standardized symbol display functionality 11 is determined based on command(s) from display switching functionality 13. That is, upon receipt of a command input thereto from display switching functionality 13, reference standardized symbol display functionality 11 initiates processing to cause display of an ARO at reference location BP. In such case, reference standardized symbol display functionality 11 may begin processing to cause display of the ARO simultaneous with receipt of the command input thereto from display switching functionality 13, or it might begin processing to cause display of the ARO after a prescribed period of time has elapsed. Where the former is the case, this will make it possible to obtain the benefit that testing can be carried out quickly; where the latter is the case, this will make it possible to obtain benefits such as reduction in the fatigue of the test subject.

Note that reference standardized symbol display functionality 11 also has functionality for stopping (extinguishing) display of ARO(s). More specifically, when in a state in which processing is being carried out for display of ARO(s), it has functionality for stopping (extinguishing) display of ARO(s) if a signal is input to reference standardized symbol display functionality 11 from input unit 3. Of course, this may be such that reference standardized symbol display functionality 11 causes display of ARO(s) to be stopped (extinguished) in a situation in which display switching functionality 13 has carried out switching from reference standardized symbol display functionality 11 to peripheral standardized symbol display functionality 12, i.e., when a command has been sent to peripheral standardized symbol display functionality 12 from display switching functionality 13.

Peripheral Standardized Symbol Display Functionality 12

Peripheral standardized symbol display functionality 12 has functionality for causing ARO(s) to be displayed at location(s) (peripheral location SP(s)) other than reference location(s) BP at display 2. More specifically, peripheral standardized symbol display functionality 12 has functionality such that when a command is sent thereto from display switching functionality 13, information (peripheral display information) including information pertaining to the location of peripheral location SP and information pertaining to the ARO to be displayed at peripheral location SP is sent to display 2, causing display of the ARO at display 2.

The information pertaining to the location of the peripheral location SP is information such as the coordinates at which the peripheral location SP is to be displayed at display 2. The peripheral location SP at which the ARO is to be displayed is determined in random fashion. For example, peripheral standardized symbol display functionality 12 might be provided with random number generation functionality, and the peripheral location SP at which the ARO is to be displayed might be determined based on random number(s) generated by this random number generation functionality. Furthermore, preestablished display map(s) or the like might be stored at storage unit 4, and the peripheral location SP at which the ARO is to be displayed might be determined based on such display map(s) or the like. Of course, random number generation functionality, display map(s), or the like might be provided at display switching functionality 13, and the peripheral location SP at which the ARO is to be displayed might be determined based on command(s) sent from such display switching functionality 13.

The information pertaining to the ARO to be displayed at peripheral location SP is information pertaining to the orientation of the ARO and/or the size of ARO to be displayed. The orientation of the ARO displayed by peripheral standardized symbol display functionality 12 is also determined in random fashion. For example, peripheral standardized symbol display functionality 12 might be provided with random number generation functionality, and the orientation of the ARO might be determined based on random number(s) generated by this random number generation functionality. Conversely, preestablished display map(s) or the like might be stored at storage unit 4, and the orientation of the ARO might be determined based on such display map(s) or the like. Of course, random number generation functionality, display map(s), or the like might be provided at display switching functionality 13, and the orientation of the ARO to be displayed might be determined based on command(s) sent from such display switching functionality 13. The size of the ARO to be displayed may be a predefined size or it may be varied so as to be of appropriate size in correspondence to the test subject. For example, AROs might be used to measure the visual acuity of the test subject, and an ARO which is somewhat larger (e.g., one step larger) than the ARO found to be the limit of the visual acuity might be employed. Furthermore, in a situation in which size is varied, it is preferred that adjustment be carried out so as to cause it to be the same size as the size of the ARO displayed at reference location BP.

The timing with which ARO(s) are caused to be displayed at peripheral location SP by peripheral standardized symbol display functionality 12 is determined based on command(s) from display switching functionality 13. That is, upon receipt of a command input thereto from display switching functionality 13, peripheral standardized symbol display functionality 12 initiates processing to cause display of an ARO at peripheral location SP. In such case, peripheral standardized symbol display functionality 12 may begin processing to cause display of the ARO simultaneous with receipt of the command input thereto from display switching functionality 13, or it might begin processing to cause display of the ARO after a prescribed period of time has elapsed. Where the former is the case, this will make it possible to obtain the benefit that testing can be carried out quickly; where the latter is the case, this will make it possible to obtain benefits such as reduction in the fatigue of the test subject.

Note that peripheral standardized symbol display functionality 12 also has functionality for stopping (extinguishing) display of ARO(s). More specifically, when in a state in which processing is being carried out for display of ARO(s), it has functionality for stopping (extinguishing) display of ARO(s) if a signal is input to peripheral standardized symbol display functionality 12 from input unit 3. Of course, this may be such that peripheral standardized symbol display functionality 12 causes display of ARO(s) to be stopped (extinguished) in a situation in which display switching functionality 13 has carried out switching from peripheral standardized symbol display functionality 12 to reference standardized symbol display functionality 11, i.e., when a command has been sent to reference standardized symbol display functionality 11 from display switching functionality 13.

Display Switching Functionality 13

Display switching functionality 13 has functionality for causing functionality for display of standardized test symbol(s) to be switched between reference standardized symbol display functionality 11 and peripheral standardized symbol display functionality 12 based on input from input unit 3. More specifically, it has functionality for determining whether reference standardized symbol display functionality 11 or peripheral standardized symbol display functionality 12 should be made to operate based on input from input unit 3.

Describing this in further detail, when reference standardized symbol display functionality 11 causes an ARO to be displayed at reference location BP, input unit 3 accepts input of the orientation of the ARO. This being the case, input unit 3 notifies display switching functionality 13 of the fact that input has occurred. Upon receipt of this notification, display switching functionality 13 causes functionality for display of ARO(s) to be switched from reference standardized symbol display functionality 11 to peripheral standardized symbol display functionality 12.

Conversely, when peripheral standardized symbol display functionality 12 causes an ARO to be displayed at peripheral location SP, input unit 3 accepts input of the orientation of the ARO. This being the case, input unit 3 notifies display switching functionality 13 of the fact that input has occurred. Upon receipt of this notification, display switching functionality 13 causes functionality for display of ARO(s) to be switched from peripheral standardized symbol display functionality 12 to reference standardized symbol display functionality 11.

Response Time Measuring Functionality 14

Response time measuring functionality 14 has functionality for measuring the time following display of an ARO by peripheral standardized symbol display functionality 12 until the orientation of the ARO is input at input unit 3.

More specifically, when peripheral display information is sent from peripheral standardized symbol display functionality 12 to display 2, simultaneous therewith a signal is sent from peripheral standardized symbol display functionality 12 to response time measuring functionality 14. Upon receipt of this signal, response time measuring functionality 14 begins measuring time. When the orientation of the ARO is eventually input at input unit 3, a signal is sent from input unit 3 to response time measuring functionality 14. This being the case, response time measuring functionality 14 stops measuring time, and sends the response time that was measured to storage unit 4. At storage unit 4, the response time is stored together with information pertaining to peripheral location SP.

Note that it is also possible for response time measuring functionality 14 to be such that it does not measure response time but instead merely stores the time at which a signal is sent from peripheral standardized symbol display functionality 12 and the time at which a signal is sent from input unit 3, and sends these times to storage unit 4.

Scotoma Determining Functionality 15

Scotoma determining functionality 15 has functionality for determining whether or not peripheral location SP is a scotoma based on the response time measured by response time measuring functionality 14. In addition, in the event that it is determined that the peripheral location SP is a scotoma, scotoma determining functionality 15 has functionality for causing information pertaining to the scotoma to be stored at storage unit 4 in association with the response time and/or information pertaining to the peripheral location SP.

Any of various methods may be employed as the method by which scotoma determining functionality 15 determines whether a scotoma is present. For example, scotoma determining functionality 15 might simply be such that when the time following display of an ARO at a peripheral location SP until the orientation has been input at input unit 3 is greater than or equal to a prescribed value, or when the orientation that was input is incorrect, a determination is made that there is a scotoma at that location.

Furthermore, a method such as the following may also be used to determine whether a scotoma is present.

For example, scotoma determining functionality 15 might be such that when the fractional number of times that the orientation of the ARO displayed at peripheral location SP does not agree with the orientation input at input unit 3 is greater than or equal to a prescribed value, a determination is made that there is a scotoma at that location regardless of how short the response time might be. More specifically, in the event that the orientation of the ARO displayed at peripheral location SP and the orientation input at input unit 3 are different (misrecognition), AROs might be displayed at the peripheral location SP where the misrecognition occurred a plurality of times at spaced-apart intervals. In addition, when the fractional number of misrecognitions (number of times that misrecognition occurred) is greater than or equal to a prescribed value, a determination might be made that there is a scotoma at that location.

Alternatively, in the event that the response time is longer than a prescribed time, scotoma determining functionality 15 might determine that there is a scotoma at that location even when the orientation of the ARO displayed at peripheral location SP agrees with the orientation input at input unit 3.

By employing such a method to determine presence of scotomas, because it will be possible to reduce occurrence of misdeterminations in which scotomas are determined to be normal areas, this will make it possible to detect scotomas with good precision.

Furthermore, when a signal is sent from peripheral standardized symbol display functionality 12 to response time measuring functionality 14, and when a signal is sent from input unit 3 to response time measuring functionality 14, a signal might also be sent to scotoma determining functionality 15. In such case, scotoma determining functionality 15 would be provided with functionality by which, if a signal is not input at scotoma determining functionality 15 from input unit 3 despite waiting at least a prescribed time after a signal has been sent from peripheral standardized symbol display functionality 12 to response time measuring functionality 14, that peripheral location SP would be determined to be a scotoma. Simultaneous therewith, scotoma determining functionality 15 would be provided with functionality by which a signal causing switching of display functionality from peripheral standardized symbol display functionality 12 to reference standardized symbol display functionality 11 would be sent to display switching functionality 13. This being the case, because it will be possible to cause testing to proceed without waiting longer than necessary for input, this will make it possible to reduce test time.

Also, in the foregoing situation, this may be such that a signal is also sent to peripheral standardized symbol display functionality 12 from scotoma determining functionality 15. In such case, it is preferred that peripheral standardized symbol display functionality 12 be provided with functionality for stopping (extinguishing) display of ARO(s) being displayed at peripheral location SP, even when no signal has been input from input unit 3, if a signal is input to peripheral standardized symbol display functionality 12 from scotoma determining functionality 15.

Note that scotoma determining functionality 15 need not necessarily be provided. For example, where information stored at storage unit 4 is subjected to processing to determine presence of scomatas following completion of visual field testing, scotoma determining functionality 15 need not be provided. Any of peripheral standardized symbol display functionality 12, display switching functionality 13, response time measuring functionality 14, and so forth may be equipped with scotoma determining functionality 15.
Standardized Symbol Size Determining Functionality 16

There is no particular limitation with regard to the size(s) of the ARO(s) displayed at reference location(s) BP and/or peripheral location(s) SP. However, from the standpoint of improving test precision, it is preferred that recognition performance of the test subject be measured immediately prior to testing, and that the size(s) of the ARO(s) to be displayed at display 2 be determined based on the results thereof. That is, it is preferred that display controller 10 have standardized symbol size determining functionality 16 by which size(s) of ARO(s) are determined.

More specifically, standardized symbol size determining functionality 16 has functionality (response time measuring functionality 16a) for measuring time (response time) from when-after information pertaining to the size and the orientation of the ARO to be displayed at reference location BP has been sent to display 2 to cause the ARO to be displayed at display 2 an ARO is displayed at display 2 until the orientation of the ARO is input at input unit 3. Note that response time measuring functionality 16a also has functionality such that, if an input signal is input from input unit 3, display of ARO(s) is stopped (extinguished), and ARO(s) of different size (or of the same size) are caused to be displayed at display 2.

Furthermore, standardized symbol size determining functionality 16 has functionality (size determining functionality 16b) for, after response time(s) have been measured for ARO(s) of a particular range of size(s), determining size(s) of ARO(s) to be used as standardized test symbol(s) based on size(s) of ARO(s) and the measured response time(s). Note that size determining functionality 16b also has functionality for causing information pertaining to determined size(s) to be sent to any of reference standardized symbol display functionality 11, peripheral standardized symbol display functionality 12, display switching functionality 13, storage unit 4, and so forth.

At size determining functionality 16b, size(s) of ARO(s) to be used as standardized test symbol(s) are determined based on the following criteria.

Response time ordinarily increases with decreasing ARO size, and decreases with increasing ARO size. However, when the ARO is greater than or equal to a certain size, response time remains more or less constant despite further increase in the size of the ARO (see circled region at FIG. 10 (A)). Accordingly, at standardized symbol size determining functionality 16, the minimum size for which the measured response time is constant is used as the standardized test symbol.

If the size of the ARO that is used as the standardized test symbol is determined in this fashion, because this will make it possible to stabilize response time, this will make it possible to improve visual field test precision.

Note that the size of the ARO that is used as the standardized test symbol is such that it is sufficient that this be a size for which the measured response time is constant. However, if the ARO is too large, because this will increase the tendency for it to fall within the field of view when displayed at peripheral regions, it is possible that the response time when displayed at peripheral regions will be shorter than the regular response time. Accordingly, it is preferred that the size of the ARO that is used as the standardized test symbol be as small as possible and be a size for which the measured response time is constant. Particularly from the standpoint of increasing test precision, it is more preferred that this be the minimum size for which the measured response time is constant.

Furthermore, in connection with measurement of response times for AROs of a particular range of sizes, the sizes of the AROs displayed at display 2 might be sequentially varied from small to large (or from large to small), or the sizes thereof might be varied in random fashion. Where sizes thereof are sequentially varied, this might be such that standardized symbol size determining functionality 16 terminates when measurement of the response time of the largest (or smallest) size has been completed. Furthermore, where sizes of the AROs are varied in random fashion, this might be such that standardized symbol size determining functionality 16 terminates when measurement of the response times for the AROs of all of the sizes within a particular range has been completed.

Moreover, at standardized symbol size determining functionality 16, when determining standardized symbol size, AROs of the same size might be displayed only once, in which case this response time would be used; or AROs of the same size might be displayed a plurality of times, in which case an average of these response times would be used. In addition, this may have functionality such that when incorrect input occurs, the ARO that is redisplayed is of the same size but has a different orientation.
Visual Field Testing A visual field test that uses the foregoing visual field test apparatus 1 will next be described.

Note that the description which follows is given in terms of an example in which testing is carried out by causing AROs of the same size to be displayed at reference location(s) BP and peripheral location(s) SP.

First, the test subject is made to face display 2, the distance (viewing distance) from display 2 to the eyes being maintained at a constant distance. For example, the viewing distance from display 2 to the eyes might be maintained at on the order of 50 cm.

Any method may be employed as the method by which the distance is maintained. However, visual field test apparatus 1 in accordance with the present embodiment is such that there is no need to block external light and there is no need to hold stationary and prevent movement of the face as is the case with conventional visual field test apparatuses. Accordingly, it is sufficient that a chinrest be provided and that the chin be made to rest on that chinrest.

Note that it is possible for display 2 to be constituted from a head-mounted display. Where this is the case, the viewing distance will automatically be held stationary.

After the face of the test subject has been arranged so as to establish a prescribed viewing distance, testing begins.

Testing might be made to begin when the test subject depresses a key on a keyboard or the like.

Note that any method may be employed as the instruction for causing testing to begin.

After testing has begun, standardized symbol size determining functionality 16 first determines size(s) of ARO(s) to be used for testing. That is, AROs of different sizes are sequentially displayed at reference location BP, and the response times for input to occur at input unit 3 are measured. In addition, standardized symbol size determining functionality 16 determines standardized symbol size based on the sizes of the AROs and the response times. After the standardized symbol size has been determined, information pertaining to the standardized symbol size that has been determined is sent to reference standardized symbol display functionality 11, peripheral standardized symbol display functionality 12, display switching functionality 13, storage unit 4, and so forth.

After information pertaining to the standardized symbol size that has been determined is input thereto, reference standardized symbol display functionality 11 executes confirmation processing to confirm reference location BP. During confirmation processing, a confirmation screen for causing the test subject to recognize reference location BP is displayed. At the confirmation screen, an ARO is displayed at the center of the screen, and display of the ARO is thereafter made to disappear for a time.

Note that where standardized symbol size determining functionality 16 is not present and/or where standardized symbol size has been determined in advance, the procedure for determining standardized symbol size might be omitted and the foregoing confirmation processing might be carried out simultaneously with the beginning of the test.

After confirmation processing has been completed, actual testing is carried out.

Figure 3:
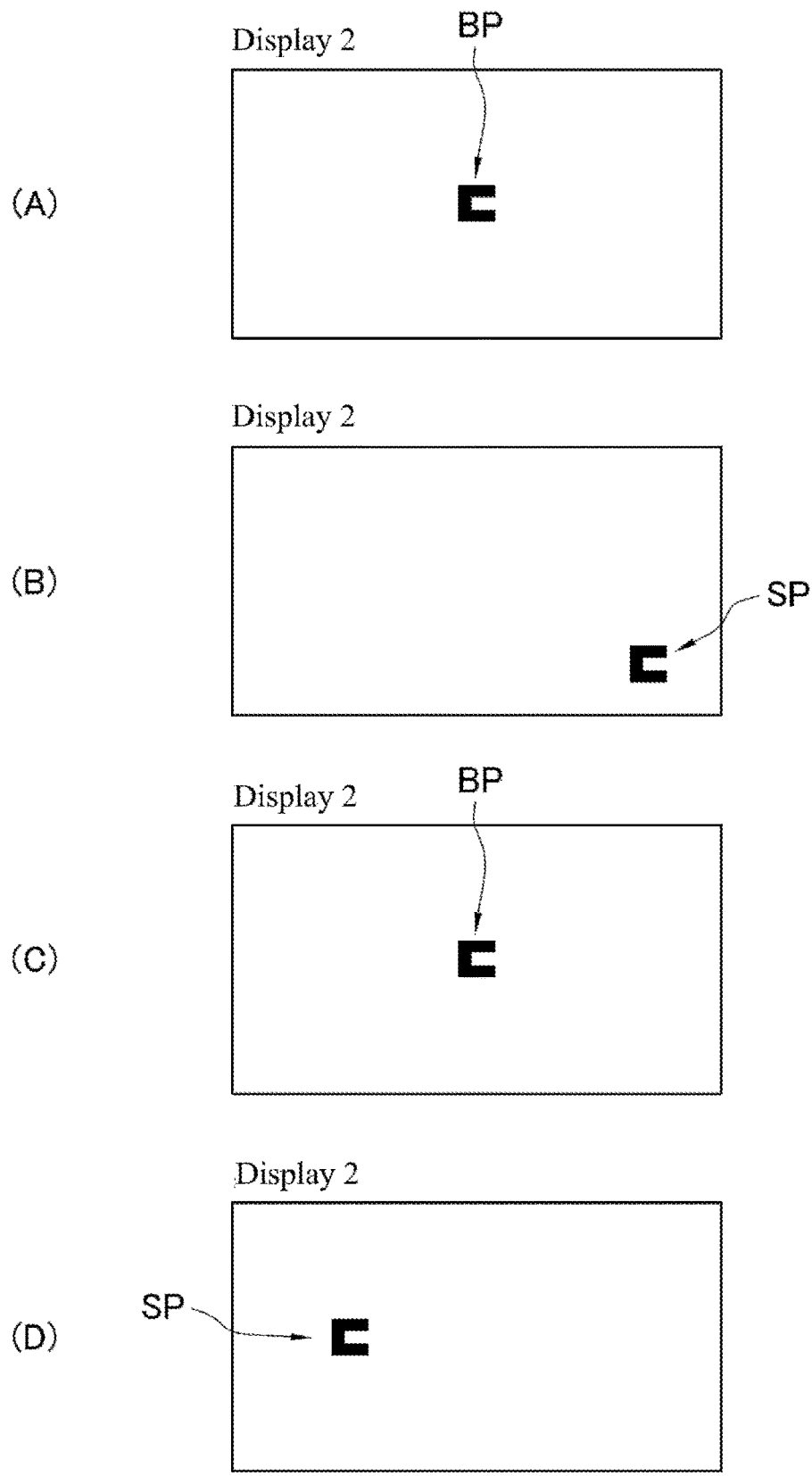
FIG. 3 Schematic explanatory diagram of a visual field measuring method using visual field measuring apparatus 1 in accordance with the present embodiment.

First, receipt of an instruction from display switching functionality 13 causes an ARO to be displayed in the center of the screen at reference location BP (FIG. 3 (A)). The test subject ascertains the orientation of the ARO displayed at reference location BP, and enters the orientation of the ARO at input unit 3.

After the orientation of the ARO has been input at input unit 3, display switching functionality 13 causes switching to occur from reference standardized symbol display functionality 11 to peripheral standardized symbol display functionality 12.

Note that if the orientation of the ARO that was input at input unit 3 is incorrect, display switching functionality 13 does not cause switching to occur from reference standardized symbol display functionality 11 to peripheral standardized symbol display functionality 12 but instead causes display by reference standardized symbol display functionality 11 to continue.

Peripheral standardized symbol display functionality 12 causes an ARO to be displayed at peripheral location SP (FIG. 3 (B)). The test subject ascertains the orientation of the ARO displayed at peripheral location SP, and enters the orientation of the ARO at input unit 3.

After the orientation of the ARO has been input at input unit 3, response time measuring functionality 14 causes response time to be measured. The response time that was measured is stored together with peripheral display information at storage unit 4. Simultaneously therewith, display switching functionality 13 causes switching to occur from peripheral standardized symbol display functionality 12 to reference standardized symbol display functionality 11. Upon so doing, reference standardized symbol display functionality 11 again causes an ARO to be displayed at reference location BP (FIG. 3 (C)).

Note that this may be such that if the orientation of the ARO that was input at input unit 3 is incorrect, display switching functionality 13 does not cause switching to occur from peripheral standardized symbol display functionality 12 to reference standardized symbol display functionality 11 but instead causes display by peripheral standardized symbol display functionality 12 to continue. Where this is the case, response time measuring functionality 14 would not measure response time but would remain in a standby state.

The test subject ascertains the orientation of the ARO displayed at reference location BP, and enters the orientation of the ARO at input unit 3. Upon so doing, display switching functionality 13 again causes switching to occur from reference standardized symbol display functionality 11 to peripheral standardized symbol display functionality 12, and peripheral standardized symbol display functionality 12 causes an ARO to be displayed at peripheral location SP (FIG. 3 (D)).

In addition, after the orientation of the ARO has been input at input unit 3, response time measuring functionality 14 causes response time to be measured, and this is stored together with peripheral display information at storage unit 4. Simultaneously therewith, display switching functionality 13 causes switching to occur from peripheral standardized symbol display functionality 12 to reference standardized symbol display functionality 11.

After the foregoing procedure has been repeated a prescribed number of times, and the response times for a prescribed number of peripheral locations SP have been measured, testing terminates.

As described above, during testing of visual field using a visual field test apparatus 1 in accordance with the present embodiment, all that is necessary is that the orientations of the AROs displayed by reference standardized symbol display functionality 11 and peripheral standardized symbol display functionality 12 be input. This being the case, it is possible to carry out testing without the need to use special equipment, and it is possible for the test subject to carry out testing by himself or herself. Accordingly, use of visual field test apparatus 1 in accordance with the present embodiment will make it possible to carry out testing of visual field easily and in a small amount of time.

Display Controller 10

The description above was given in terms of an example in which display controller 10 had a plurality of independent functionalities including reference standardized symbol display functionality 11. However, display controller 10 might be made to have only a single display functionality, and this display functionality might be equipped with all of the functionalities described above including reference standardized symbol display functionality, peripheral standardized symbol display functionality, and display switching functionality. For example, this might be such that AROs are displayed in alternating fashion at reference location BP and at peripheral location SP in response to input from input unit 3.

Furthermore, response time measuring functionality 14 need not necessarily be independently provided. One of the foregoing display functionalities (display switching functionality 13, peripheral standardized symbol display functionality 12, etc.) might be equipped with the functionality of response time measuring functionality 14.

Map Forming Functionality

Furthermore, visual field test apparatus 1 may have map forming functionality for causing display of test results in the form of a map (scotoma map). If results are displayed in the form of a scotoma map, because this will make it possible to visually grasp the distribution of scotomas, this facilitates use thereof for diagnosis of diseases.

In particular, if in addition to carrying out the foregoing testing of visual field with respect to only one eye, testing is carried out with respect to both eyes (i.e., testing in which AROs are confirmed using both eyes), and a scotoma map is formed and displayed based on both sets of results, this will make it possible to better increase the precision with which diseases can be diagnosed.

Other Examples of Determining Whether Scotoma(s) are Present

While determination of whether or not scotoma(s) are present by scotoma determining functionality 15 may be carried out using a determination method as described above, use of a determination method such as the following will make it possible to more precisely determine whether scotoma(s) are present.

First, it is thought that the aforementioned response time will ordinarily include the following times.
(1) Standardized symbol discovery time (a)
(2) Gaze relocation (saccade) time (b)
(3) Gap determination time (c)
(4) Key pressing time (d)

This being the case, response time T1 can be found from the following equation.

$$T1 = \text{Standardized symbol discovery time } (a) + \text{gaze relocation (saccade) time } (b) + \text{gap determination time } (c) + \text{key pressing time } (d)$$

Of the components making up response time T1, standardized symbol discovery time (a) and gaze relocation (saccade) time (b) will vary depending on the location at which the ARO is displayed. That is, regardless of whether or not there is a scotoma present, response time T1 will vary depending on distance from reference location BP. Stating this differently, when the distance from reference location BP to peripheral location SP is large, there is a possibility that a determination will be made that there is a scotoma even when a scotoma is not present unless the response time T1 at which it is determined that there is a scotoma is set to an appropriate value.

Here, it is thought that each of standardized symbol discovery time (a), gaze relocation (saccade) time (b), gap determination time (c), and key pressing time (d) will vary from person to person. This being the case, the response time T1 at which it is determined that there is a scotoma cannot be set to be the same value for a test subject for whom these times are long as it is set to for a test subject for whom these time are short.

On the other hand, it is thought that once the ARO has been discovered, gap determination time (c) and key pressing time (d) will be more or less the same for the same test subject. Furthermore, because it is thought that standardized symbol discovery time (a) will be more or less zero so long as there is no scotoma present, it is thought that response time T1 will vary as a function of gaze relocation (saccade) time (b). In addition, it is thought that gaze relocation (saccade) time (b) will vary as a function of the angle (angular deviation θ) from reference location BP to the peripheral location SP at which the ARO is displayed. This being the case, so long as there is no scotoma present, it can be assumed that gaze relocation (saccade) time (b), i.e., response time T1, will be in a linear relationship with respect to angular deviation θ.

Such relationship between response time T1 and angular deviation θ can be determined by performing linear approximation through use of a graph in which angular deviation θ is plotted on the horizontal axis and response time T1 is plotted on the vertical axis. That is, by using this, it will be possible obtain a formula (i.e., a linear-regression line, least-squares line, or other such best-fit line) that is an approximation of the relationship between response time T1 and angular deviation θ.

Note that there is no particular limitation with respect to the method by which the graph is used to perform linear approximation and the approximation formula is extracted therefrom, it being possible to employ any of the various known methods therefor.

If the response time that is actually measured is very different from response time T1 obtained from this approximation formula, it can be assumed that this is a location at which it is difficult to discover the ARO, i.e., a scotoma.

As described above, it is preferred that scotoma determining functionality 15 have functionality for determining whether scotoma(s) are present in which the criterion for determination is a best-fit line obtained by performing linear approximation on a graph on which ARO location and response time are plotted. In such case, because it will be possible to compensate for differences in response time depending on the location at which the ARO is displayed, this will make it possible to more accurately determine whether scotoma(s) are present.

Note that angular deviation θ can be calculated based on the viewing distance and the distance from reference location BP to the peripheral location SP.

Furthermore, instead of the relationship between response time T1 and angular deviation θ, the distance from reference location BP to peripheral location SP can be used to produce the graph. That is, even where linear approximation is performed on a graph in which distance from reference location BP to peripheral location SP is plotted on the horizontal axis and response time T1 is plotted on the vertical axis, it will be possible by performing linear approximation on the graph to obtain an approximation formula expressing the relationship between response time T1 and distance. Accordingly, the functionality for determining whether scotoma(s) are present may be such that the criterion for determination is this approximation formula.

The aforementioned angular deviation θ and distance from reference location BP to the peripheral location SP correspond to the standardized test symbol offset information that is recited in the claims.

Scotoma Separation Determination

Furthermore, when obtaining the aforementioned approximation formula, if data which includes scotoma(s) is used in creating the approximation formula, there is a possibility that the approximation formula that is obtained will be different from the approximation formula that would have been obtained had only data which does not include scotoma(s) been used. Accordingly, for more precise detection of scotoma(s), it is preferred that the following processing be carried out.

First, clustering is employed to separate the data that is obtained into a linear portion (i.e., non-scotoma portion) and a scotoma portion (hereinafter "scotoma candidate(s)"). Clustering may be carried out by any known method. For example, an EM algorithm, K-means technique, or the like might be employed to separate this into a non-scotoma portion and scotoma candidate(s).

Next, a method similar to the method by which an approximation formula was extracted as described above is used to extract a linear-regression line, least-squares line, or other such best-fit line from the non-scotoma portion. While this best-fit line may be extracted by a method similar to the method by which an approximation formula was extracted as described above, there is no particular limitation with respect thereto.

After the best-fit line has been extracted, the scotoma dividing line is extracted. The scotoma dividing line may be extracted using any of various methods. For example, a line which is parallel to the foregoing best-fit line and which passes through the space intermediate between data separated into scotoma candidate(s) and data separated into a non-scotoma portion might be employed as the scotoma dividing line.

After such a scotoma dividing line has been found, scotoma(s) may be found by carrying out determination in such fashion that any location having a response time greater than that indicated by the scotoma dividing line is a scotoma.

Method Using Marriotte Blind Spot

When the scotoma dividing line is being extracted, it is preferred that the Marriotte blind spot, which is definitely a scotoma, be used. In such case, a line which is parallel to the foregoing best-fit line and which satisfies one of the following conditions may be employed as the scotoma dividing line.

1) The line which intercepts the time axis at the lowest value which is a line parallel to a best-fit line passing through data categorized as scotoma candidate(s) and within the scotoma determination region 2) The line which intercepts the time axis at the largest value which is a line lower than the line obtained by the method at 1) and parallel to a best-fit line passing through data categorized as the non-scotoma portion Scotomas may be found with good precision by establishing a scotoma determination region as described above, and, where a zone in which the Marriotte blind spot can be assumed to be present is located within that zone, finding the scotoma dividing line, and carrying out determination in such fashion that any location having a response time greater than that indicated by the scotoma dividing line is a scotoma.

In particular, employment of a scotoma dividing line obtained by the method at 2) will make it possible to more precisely find scotomas.

Removal of Perimeter Portion

Here, because image distortion and the like tend to occur at the perimeter portion of display 2, making it difficult for the test subject to visually perceive the ARO, there is a possibility that response time will be large and that a scotoma will be mistakenly determined to be present despite the fact that no scotoma is present. Accordingly, the zone located at the perimeter portion of display 2 may be removed from the zone which is investigated for presence of scotoma(s). There is no particular limitation with respect to the range of the zone (removed zone) that is removed from the zone which is investigated for presence of scotoma(s), it being sufficient that this be set as appropriate in correspondence to characteristics of the equipment at display 2. For example, where display 2 is an HMD screen, the removed zone may consist of only those pixels that are located at the outermost perimeter. Furthermore, where different equipment is employed, the removed zone might be a plurality of pixels (e.g., on the order of 2 to 5 pixels) from the outer perimeter.

Still More Examples of Determining Whether Scotoma(s) are Present

As another, simple method, single-eye scotoma(s) may be found based on differences between results of measurements performed with both eyes versus results of measurements performed with one eye. That is, because when performing testing with both eyes a scotoma in one eye is compensated for by information from the other eye, a location for which the two give different results may be determined to be a scotoma. Accordingly, scotoma determining functionality 15 may compare data at respective locations as measured with both eyes and data at respective locations as measured with one eye, and may determine that a scotoma is present at locations where there is a difference therebetween.

Working Example 1

It was confirmed that detection of scotomas can be carried out using a visual field test apparatus in accordance with the present invention.

During testing, at a visual field test apparatus in accordance with the present invention, an application was created that had functionality equivalent to the aforementioned display controller, and this application was used to cause a display apparatus to display AROs. In addition, a test subject was asked to use the cursor keys of a keyboard to input the orientation of the ARO that was displayed at the display apparatus, the response time until receipt of input from the cursor keys was measured, that response time data was analyzed, and a scotoma map was created.

The detailed test procedure was as indicated below.
1) A prestimulus (ARO) indicating the center of the screen (reference location) was displayed for 500 msec.
2) A nonstimulatory screen (screen on which nothing is displayed) was displayed for 500 msec.
3) An ARO was displayed at the reference location.
4) Following input of the orientation of the ARO, the ARO at the reference location was made to disappear, and an ARO was displayed at a peripheral location.
5) Following input of the orientation of the ARO, the ARO at the peripheral location was made to disappear, and a nonstimulatory screen was displayed for 1000 msec.
6) The procedure at the foregoing 2 through 5 was repeated 250 times, and testing was concluded.

The ARO and the specifications of the display apparatus employed were as follows.

Display Apparatus
Liquid crystal display: LCD-MF222FBR-T manufactured by IO-DATA
Pixels: 1920 (H)×1080 (V)
Pixel pitch: 0.24825 (H)×0.24825 (V)
Display area: 476.64 mm (H)×268.11 mm (V)
Reproducible colors: 16,770,000 colors
Visual field angle: Vertical 160°/horizontal 170°
Maximum brightness: 260 cd/m$^2$
Response speed: 5 ms
Brightness (cd/m$^2$): White region 140.8; black region 3.3
Michelson contrast: 0.954
ARO
Vertical/Horizontal Size: 12 Pixels×12 Pixels (Notch Size: 4 Pixels)

Figure 5:
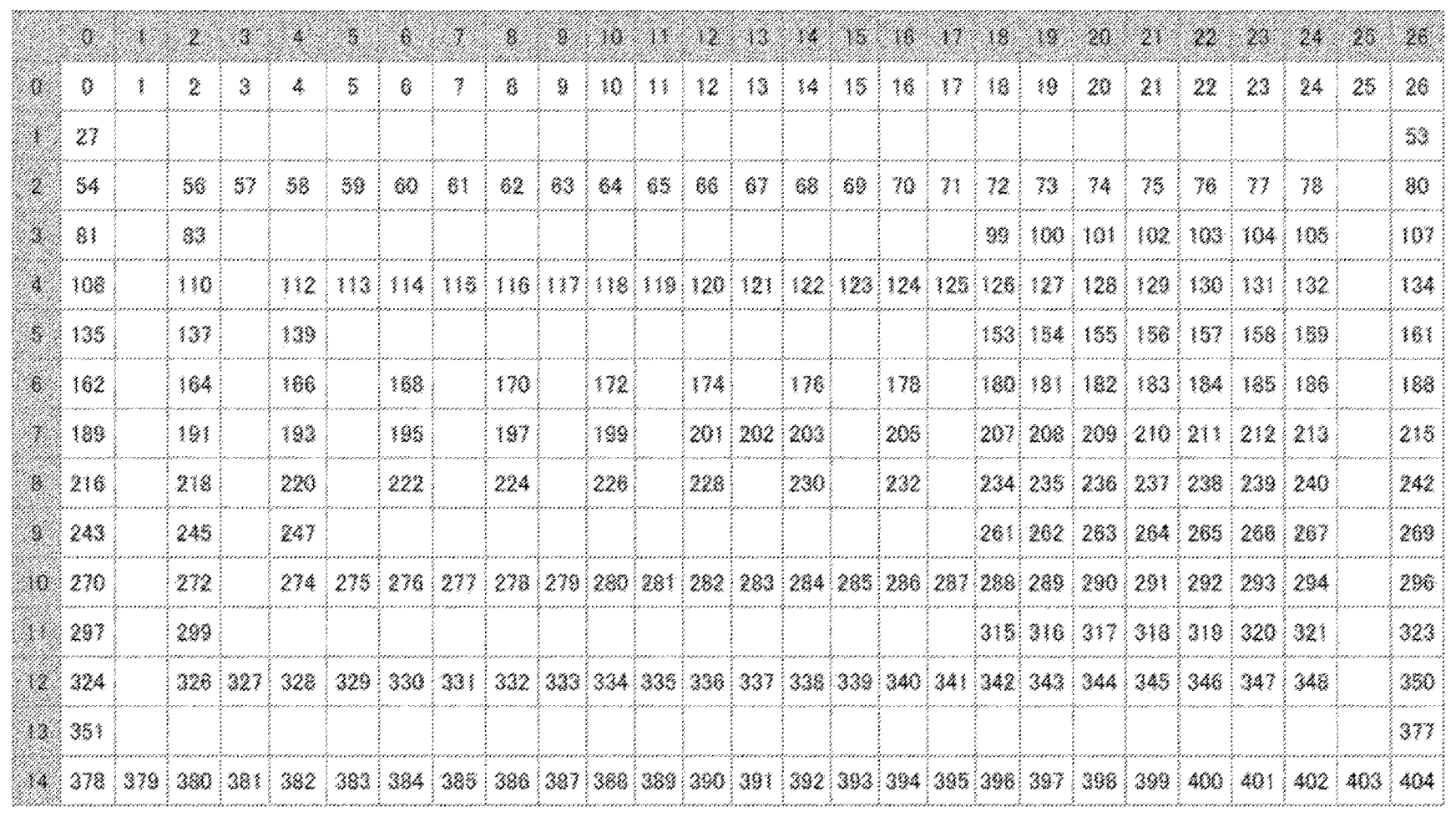

Locations at which measurement for scotomas was performed, i.e., locations at which the display apparatus was made to display AROs, were such that there were 405 points, the screen being divided into 27 sectors in the height direction and being divided into 15 sectors in the width direction (see FIG. 5). Note that, so as to make it possible to definitively detect the Marriotte blind spot, during each test trial, AROs were displayed with increased density, in a display pattern that included 250 points of the 405 total points, within a region surrounding the Marriotte blind spot.

Note that determination of whether scotoma(s) were present was carried out such that the criterion for determination was the best-fit line obtained by performing linear approximation on a graph in which angular deviation theta was plotted on the horizontal axis and response time T1 was plotted on the vertical axis. That is, locations at which response time T1 differed substantially (deviation greater than or equal to 500 ms) from the best-fit line were determined to be scotomas.

Testing was performed on sixteen visually unimpaired persons of ages 18 to 24 years.

Ambient conditions of the room in which testing was carried out were such that it was illuminated, and a chinrest was used to maintain a constant viewing distance (distance from the face of the test subject to the display apparatus) of 50 cm.

Note that testing of the right eye and of both eyes was performed under naked-eye conditions (but where corrective lenses such as contact lenses or eyeglasses were used, these were employed). Note that when carrying out measurements on the right eye, the left eye was covered with gauze.

Exemplary results are shown in FIGS. 6 through 9.

Figure 6:
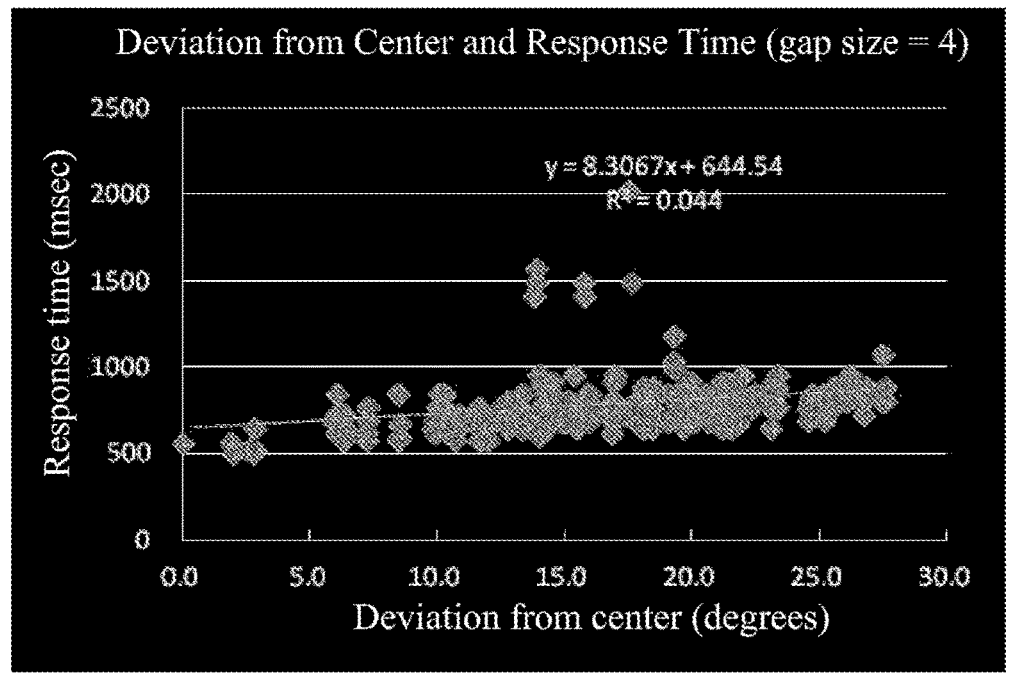
FIG. 6 Drawings showing results of testing.
Figure 6:
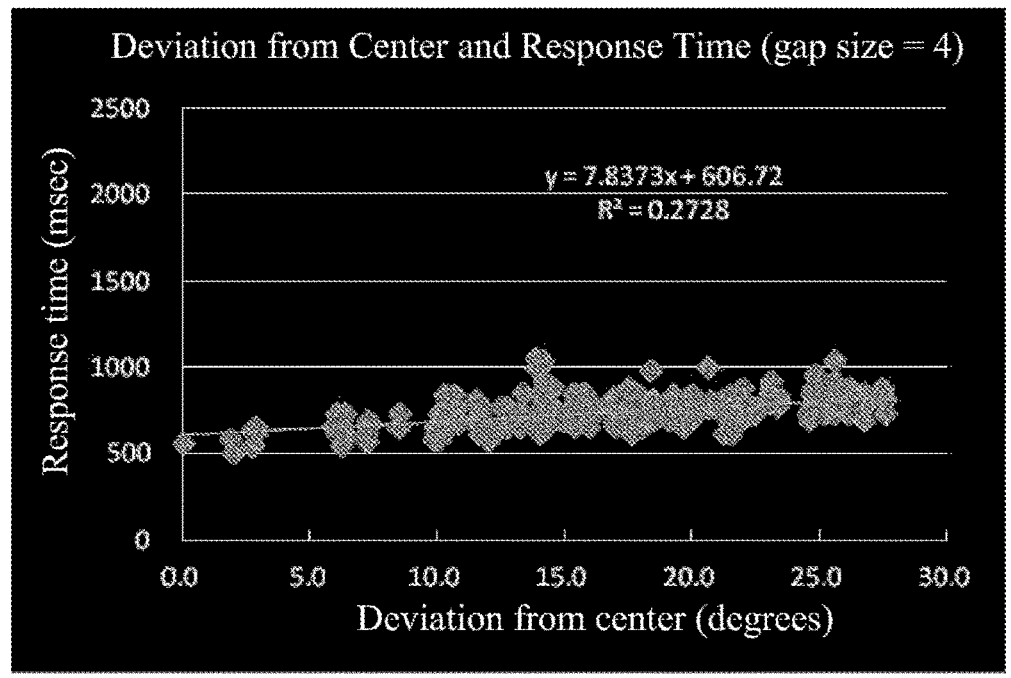
Figure 7:
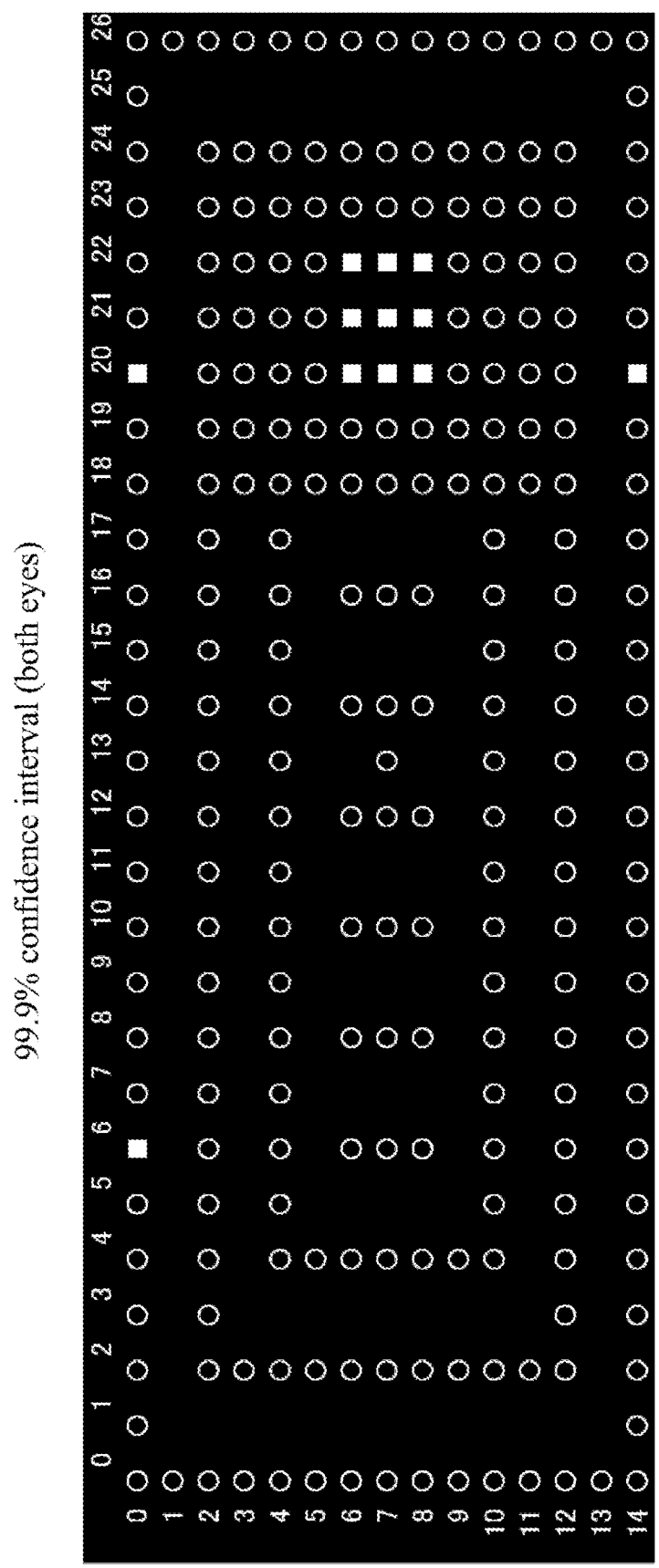
FIG. 7 Drawing showing results of testing.

As shown in FIG. 6, with a normal test subject, response times were distributed more or less in the vicinity of the best-fit line. It was confirmed that any scotomas of the test subject that could be inferred based on the best-fit line were more or less concentrated in the vicinity of the Marriotte blind spot (FIG. 7).

Figure 8:
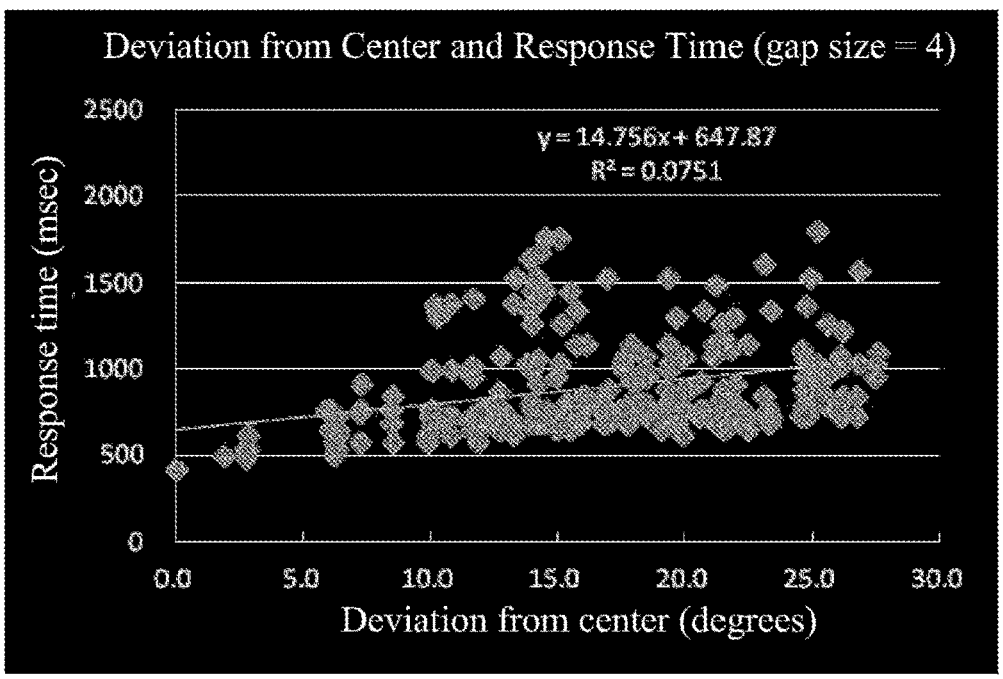
FIG. 8 Drawings showing results of testing.
Figure 8:
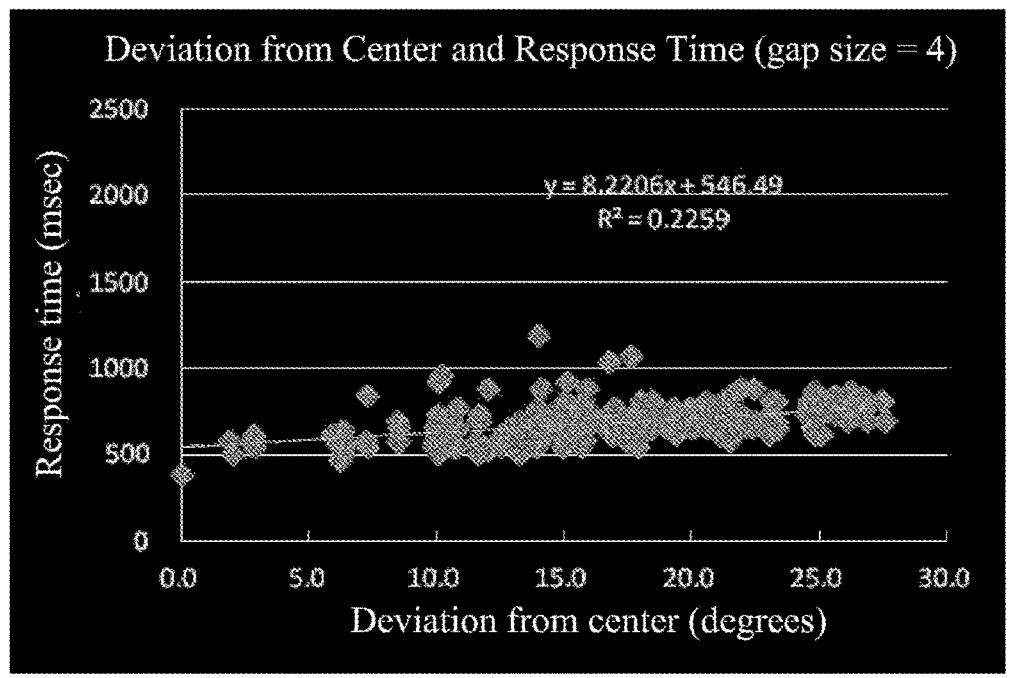
Figure 9:
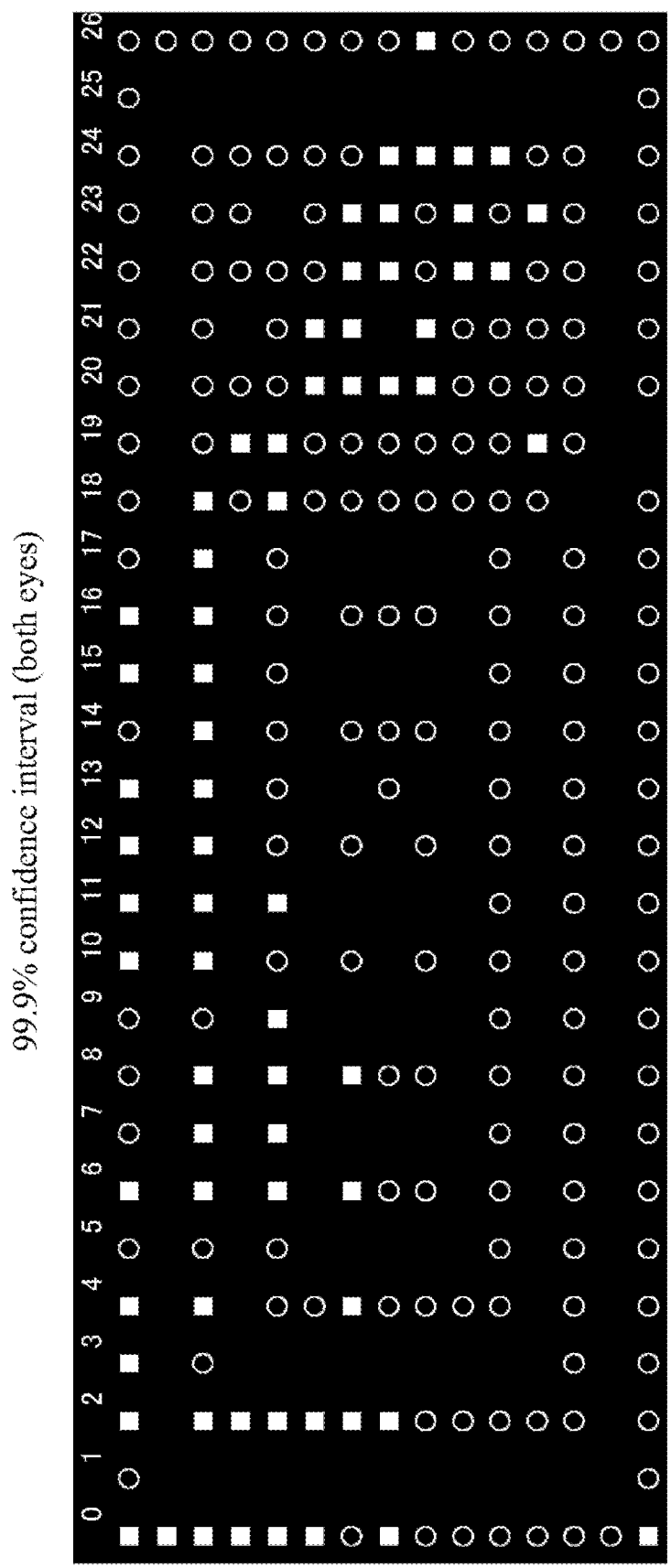
FIG. 9 Drawing showing results of testing.

On the other hand, as shown in FIG. 8, with another test subject, response times substantially distant from the best-fit line were present in scattered fashion. For this test subject, there were many scotomas that could be inferred based on the best-fit line that were distributed so as to not to be in the vicinity of the Marriotte blind spot (FIG. 9), and it was speculated that some abnormality existed. Upon receiving an in-depth scotoma examination by an ophthalmologist using existing medical equipment at a later date, this test subject was found to have a congenital retinal abnormality.

Based on the foregoing results, it was confirmed that the visual field measuring method of the present invention makes it possible to carry out testing in simple fashion and with maintenance of the required precision, and is potentially capable of being employed as a test method permitting determinations to be made with respect to diseases.

Working Example 2

The method for separating scotomas was changed, and it was confirmed that scotomas could be more appropriately separated. Determination of whether scotomas were present was performed on thirty-two visually unimpaired persons of ages 21 to 25 years by carrying out measurements in similar fashion as at Working Example 1 except for the points listed below.

Note that an HMZ-T3 head-mounted display manufactured by SONY was used as display apparatus, and a joy stick was used as input device.

Figure 10:
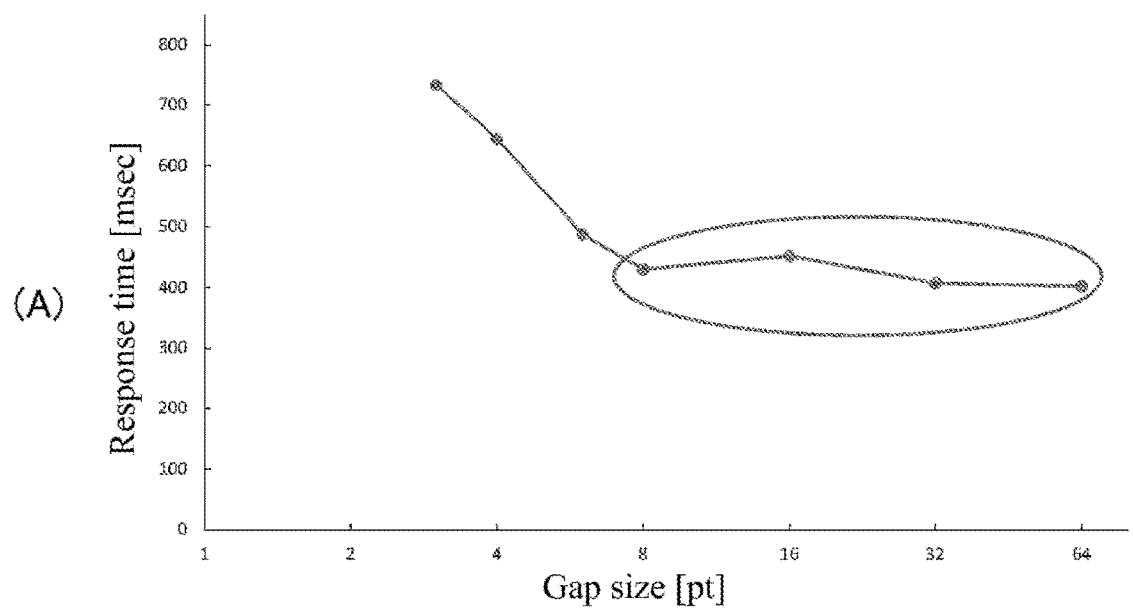
FIG. 10 (A) is a drawing showing relationship between standardized symbol size and response time; (B) is a drawing showing an example of a scotoma determination region within a displayed map.
Figure 10:
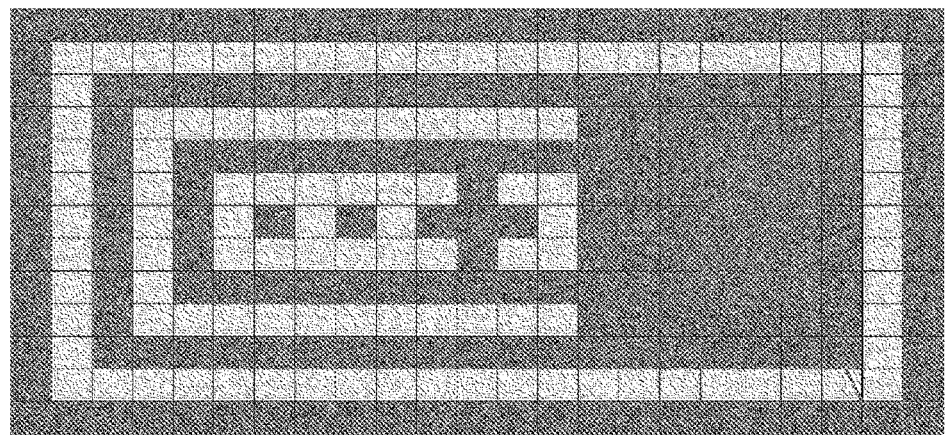

Note that, of the locations at which the AROs were displayed at the display apparatus, the locations indicated at FIG. 10 (B) were taken to be the scotoma determination region.

First, clustering using an EM algorithm was employed to separate measurement results data into scotoma candidate(s) and a non-scotoma portion.

Having done this, a linear-regression line for the non-scotoma portion was determined, and scotoma dividing lines were thereafter extracted.

Scotoma dividing lines satisfying the following two conditions were extracted, and scotoma determination based on each was compared.

1) The line which intercepts the time axis at the lowest value which is a line parallel to a best-fit line passing through data categorized as scotoma candidate(s) and within the scotoma determination region 2) The line which intercepts the time axis at the largest value which is a line lower than the line obtained by the method at 1) and parallel to a best-fit line passing through data categorized as the non-scotoma portion Note that the scotoma determination region was set so as to include the zone within which the Marriotte blind spot was assumed to be present (see FIG. 10 (B)).

Note that the average scotoma detection rate (recall) is calculated as the fraction of scotoma candidate(s) included within displayed locations that were included within the scotoma determination region.

Furthermore, average precision (precision) is calculated as the fraction of displayed locations determined to be scotomas that were included within the scotoma determination region.

Figure 11:
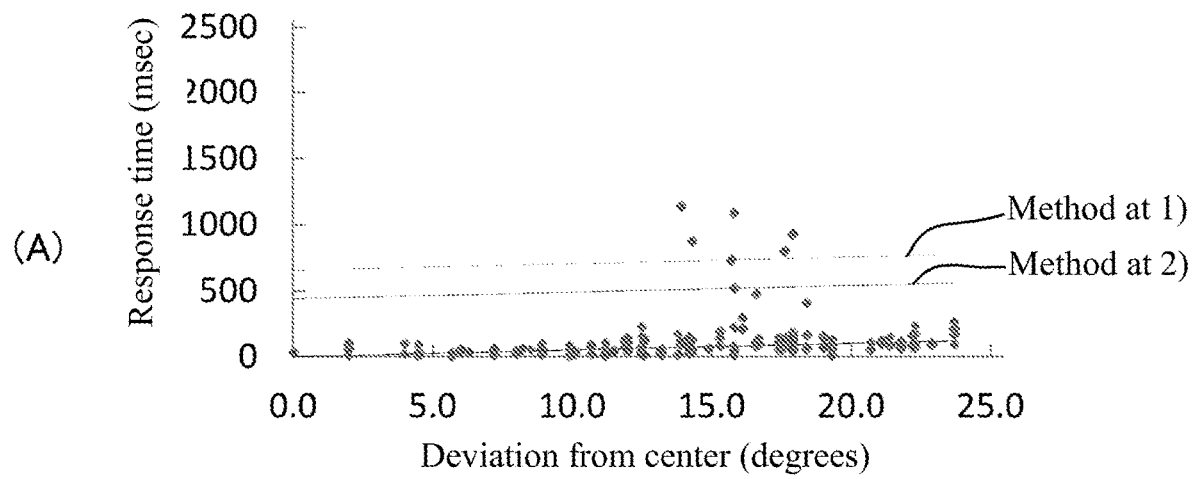
FIG. 11 (A) is a drawing showing a scotoma determination line; (B) shows tables presenting results of testing using the method at 1) and the method at 2) in Working Example 2.
Figure 12:
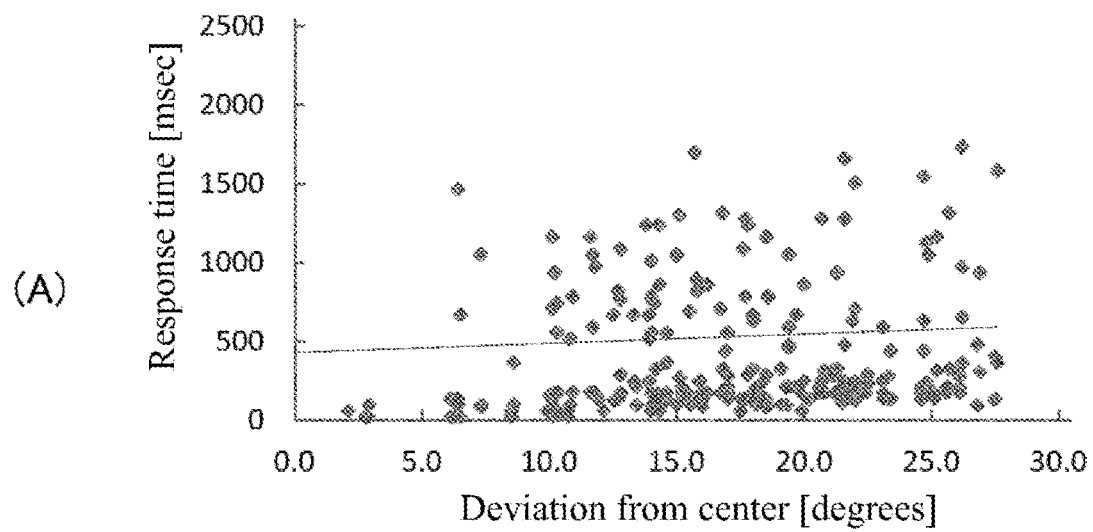
FIG. 12 Drawings showing results obtained using the method at 1) in Working Example 2.
Figure 12:
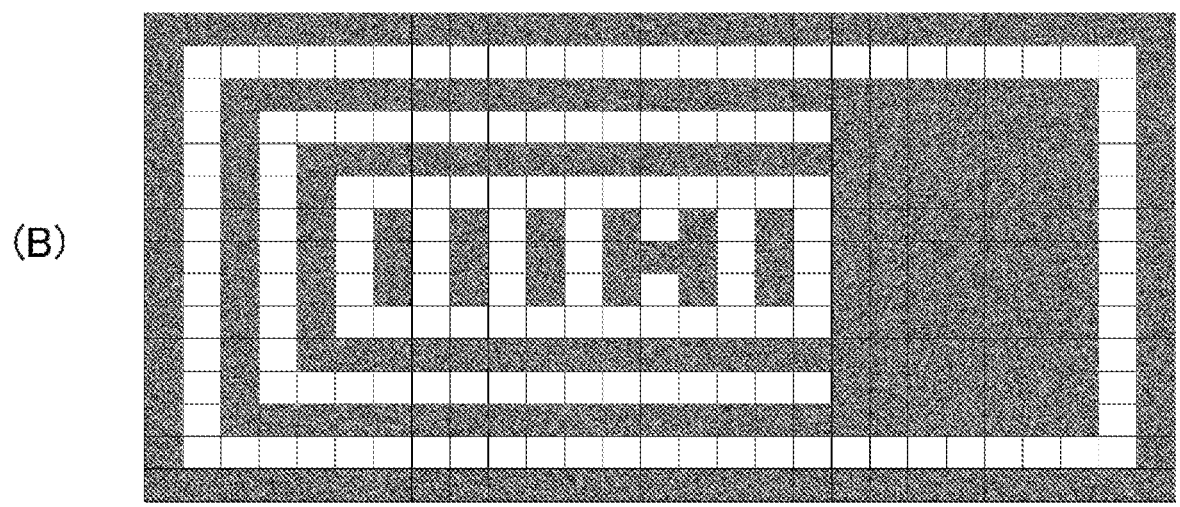

Results are shown in FIG. 11 through FIG. 12.

As shown at FIG. 11 (A), depending on whether the method at 1) or the method at 2) was employed, there was a difference in the scotoma dividing line, and there were also differences in the average scotoma detection rate and the average precision (FIG. 11 (B)). Based on this, it was found that depending on which method was used as the method for extracting the scotoma dividing line, there was a difference in what was determined to be a scotoma.

Note that both the arithmetic mean and vector composition were employed as techniques for obtaining the statistical mean at the best-fit line when extracting the scotoma dividing line, but regardless of whether the method at 1) or the method at 2) was employed it was found that there was practically no difference between these methods.

For the test subject who had a visual field abnormality in the right eye, results of testing using a Humphrey visual field analyzer were compared with the method at 1).

Figure 13:
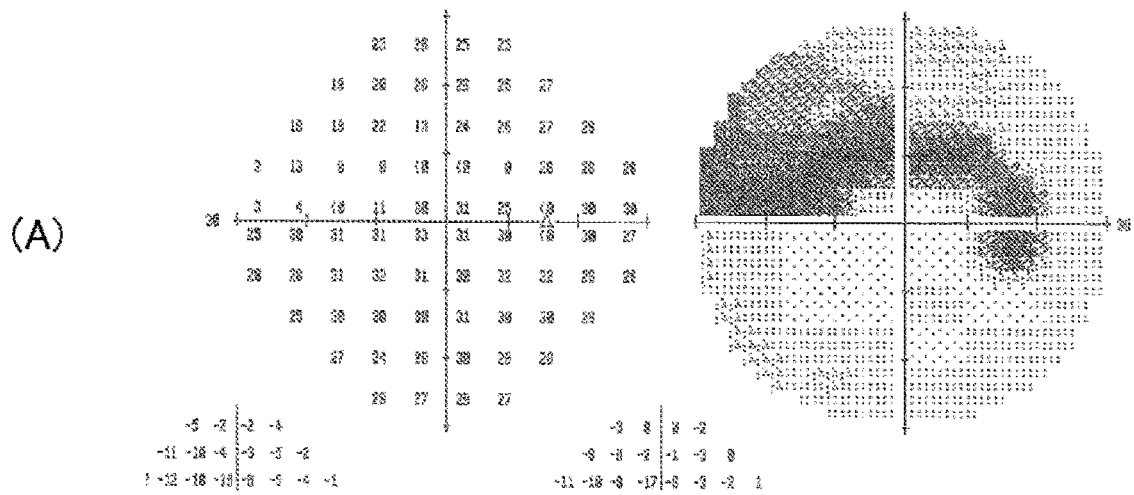
FIG. 13 Drawings showing results of testing using a Humphrey visual field analyzer.
Figure 13:
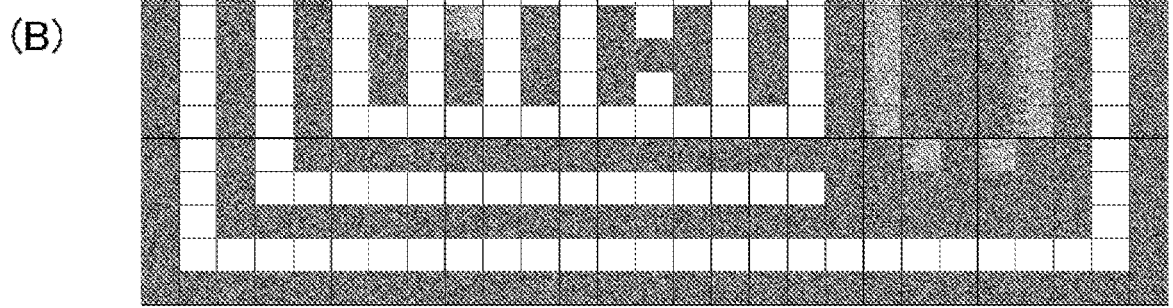

As shown in FIG. 12 and FIG. 13, it can be seen that the results obtained using the method at 1) are more or less equivalent to the results of testing using the Humphrey visual field analyzer. That is, this confirms that by using a method in accordance with the present invention it is possible through use of a simple test to detect scotomas with a precision that is equivalent to that obtained with a Humphrey visual field analyzer.

INDUSTRIAL UTILITY

A visual field measuring apparatus in accordance with the present invention is suitable as an apparatus for measuring scotomas for use in making determinations with respect to any of a variety of diseases including glaucoma, pigmentary degeneration of the retina, diabetic retinopathy, detachment of the retina, and macular degeneration.

Furthermore, an optotype in accordance with the present invention is suitable as a standardized test symbol for testing of minimum separable acuity.

EXPLANATION OF REFERENCE NUMERALS

1 Visual field test apparatus
2 Display
3 Input unit
4 Storage unit
10 Display controller
11 Reference standardized symbol display functionality
12 Peripheral standardized symbol display functionality 13 Display switching functionality
14 Response time measuring functionality
15 Scotoma determining functionality
16 Standardized symbol size determining functionality
16*a* Response time measuring functionality
16*b* Size determining functionality

The invention claimed is:

1. A visual field measuring method in which standardized test symbols are sequentially displayed at a display to measure visual field, the visual field measuring method being characterized in that it comprises:
   a reference standardized symbol display operation in which a standardized test symbol is displayed at a reference location provided at a center of the display;
   a reference input operation in which a test subject is made to input the fact that the standardized test symbol displayed at said reference standardized symbol display operation has been recognized;
   a peripheral standardized symbol display operation in which, following the input of the fact that the standardized test symbol was recognized at said reference input operation, a standardized test symbol is displayed at a peripheral location which is different from the reference location; and
   a peripheral input operation in which the test subject is made to input the fact that the standardized test symbol displayed at said peripheral standardized symbol display operation has been recognized;
   wherein from the reference standardized symbol display operation to the peripheral input operation is executed in repeated and sequential fashion, and a response time from when the standardized test symbol is displayed at the peripheral standardized symbol display operation to when the input is performed by the test subject at the peripheral input operation is measured;
   the standardized test symbol displayed at the peripheral standardized symbol display operation is a standardized test symbol for testing visual acuity;
   the test subject is made to input an orientation of the standardized test symbol at the peripheral standardized symbol display operation;
   when a fractional number of times that the orientation input by the test subject at the peripheral input operation does not match the orientation of the standardized test symbol displayed at the peripheral standardized symbol display operation is greater than or equal to a prescribed value, or
   when the orientation input by the test subject at the peripheral input operation matches the orientation of the standardized test symbol displayed at the peripheral standardized symbol display operation but the response time is greater than or equal to a prescribed time,
   said peripheral location is determined to be a scotoma; and
   a criterion for the determination as to whether the scotoma is present is a best-fit line obtained by performing linear approximation on a graph plotting the response time in such fashion that offset information pertaining to the standardized test symbol displayed at the peripheral standardized symbol display operation is plotted on a horizontal axis and the response time is plotted on a vertical axis.

2. The visual field measuring method according to claim 1 characterized in that
   data from which scotoma candidates have been removed is employed for the best-fit line;
   a scotoma dividing line which is parallel to the best-fit line is extracted based on the scotoma candidates; and
   a location among the scotoma candidates for which the response time is greater than that indicated by the scotoma dividing line is determined to be a scotoma.

3. The visual field measuring method according to claim 2 characterized in that
   data for a portion of the scotoma candidates that are located in the Marriotte blind spot is used to extract a scotoma determination line.

4. The visual field measuring method according to claim 1 characterized in that
   standardized test symbols of differing size are displayed at the reference location to test visual acuity, and response times from when the standardized test symbols are displayed until when directions of the standardized test symbols are input by the test subject are measured; and
   a size of the standardized test symbol to be used to test visual field is determined based on a relationship between the sizes of the standardized test symbols and the response times.

5. The visual field measuring method according to claim 1 characterized in that
   the standardized test symbol is an optotype formed from a pair of mutually parallel lines, and a single connecting line that connects mutually opposed end edges of the lines making up said pair of parallel lines;
   wherein the pair of parallel lines are formed so as to be of the same length;
   wherein the connecting line is perpendicular to the pair of parallel lines; and
   wherein widths of the lines making up the pair of parallel lines, width of a gap between the pair of parallel lines, and width of the connecting line are formed so as to all be the same length.

6. The visual field measuring method according to claim 5 characterized in that
   the standardized test symbol is formed in such fashion that lengths of the lines making up the pair of parallel lines, and distance between outer edges of the pair of parallel lines, are the same length.

7. The visual field measuring method according to claim 5 characterized in that
   a ratio between lengths and widths of the lines making up the pair of parallel lines is chosen so as to be 2:1 to 5:1.

8. The visual field measuring method according to claim 1 characterized in that
   the standardized test symbol displayed at the reference standardized symbol display operation is a standardized test symbol for testing visual acuity; and
   the test subject is made to input an orientation of the standardized test symbol at the reference standardized symbol display operation.

9. A visual field measuring apparatus characterized in that it comprises:
   a display that displays a standardized test symbol;
   an input unit that accepts input from a test subject of the fact that the standardized test symbol displayed by said display has been recognized; and
   a display controller that controls timing and location at which the standardized test symbol is displayed by the display;
   wherein said display controller comprises
      reference standardized symbol display functionality that causes a standardized test symbol to be displayed at a reference location at the display;

peripheral standardized symbol display functionality that causes a standardized test symbol to be displayed at a peripheral location which is different from the reference location at the display;

display switching functionality that performs switching between the reference standardized symbol display functionality and the peripheral standardized symbol display functionality based on a signal from the input unit; and response time measuring functionality that measures a time from when the peripheral standardized symbol display functionality causes the standardized test symbol to be displayed until when the test subject enters the input at the input unit;

the standardized test symbol displayed at the peripheral location of the display by the peripheral standardized symbol display functionality is a standardized test symbol for testing visual acuity;

the input unit is constituted so as to accept input of an orientation of the standardized test symbol by the test subject who recognizes the standardized test symbol displayed at the peripheral location of the display by the peripheral standardized symbol display functionality;

the display controller has scotoma determining functionality for making a determination as to whether a scotoma is present based on the input which is entered at the input unit;

said scotoma determining functionality has scotoma determining functionality such that when a fractional number of times that the orientation input at the input unit when the standardized test symbol is displayed at the peripheral location does not match the orientation of the standardized test symbol displayed by means of the peripheral standardized symbol display functionality displayed by the peripheral standardized symbol display functionality is greater than or equal to a prescribed value, or when the orientation input at the input unit when the standardized test symbol is displayed at the peripheral location matches the orientation of the standardized test symbol displayed by the peripheral standardized symbol display functionality but a measured time measured by the response time measuring functionality is greater than or equal to a prescribed time, the peripheral location is determined to be a scotoma; and a criterion for the determination as to whether the scotoma is present is a best-fit line obtained by performing linear approximation on a graph plotting the measured response time in such fashion that offset information pertaining to the standardized test symbol displayed by the peripheral standardized symbol display functionality is plotted on a horizontal axis and the response time is plotted on a vertical axis.

10. The visual field measuring apparatus according to claim 9 characterized in that the scotoma determining functionality has functionality such that data from which scotoma candidates have been removed is employed for the best-fit line;

a scotoma dividing line which is parallel to the best-fit line is extracted based on the scotoma candidates; and a location among the scotoma candidates for which the response time is greater than that indicated by the scotoma dividing line is determined to be a scotoma.

11. The visual field measuring apparatus according to claim 10 characterized in that the scotoma determining functionality has functionality such that data for a portion of the scotoma candidates that are located in the Marriotte blind spot is used to extract a scotoma determination line.

12. The visual field measuring apparatus according to claim 9 characterized in that the display controller is equipped with standardized symbol size determining functionality for determining sizes of the standardized test symbols displayed at the reference location and the peripheral location; and said standardized symbol size determining functionality has response time measuring functionality for causing standardized test symbols of differing size to be displayed at the reference location to test visual acuity, and measuring response times from when said standardized test symbols are displayed until when directions of said standardized test symbols are input by the test subject; and size determining functionality for causing a size of the standardized test symbol that will be used to test visual field to be determined based on a relationship between the sizes of the standardized test symbols and the response times measured by said response time measuring functionality.

13. The visual field measuring apparatus according to claim 9 characterized in that the standardized test symbol is an optotype formed from a pair of mutually parallel lines, and a single connecting line that connects mutually opposed end edges of the lines making up said pair of parallel lines;

wherein the pair of parallel lines are formed so as to be of the same length;

wherein the connecting line is perpendicular to the pair of parallel lines; and wherein widths of the lines making up the pair of parallel lines, width of a gap between the pair of parallel lines, and width of the connecting line are formed so as to all be the same length.

14. The visual field measuring apparatus according to claim 13 characterized in that the standardized test symbol is formed in such fashion that lengths of the lines making up the pair of parallel lines, and distance between outer edges of the pair of parallel lines, are the same length.

15. The visual field measuring apparatus according to claim 13 characterized in that a ratio between lengths and widths of the lines making up the pair of parallel lines is chosen so as to be 2:1 to 5:1.

16. The visual field measuring apparatus according to claim 9 characterized in that the standardized test symbol displayed at the reference location of the display by the reference standardized symbol display functionality is a standardized test symbol for testing visual acuity; and the input unit is constituted so as to accept input of an orientation of the standardized test symbol by the test subject who recognizes the standardized test symbol displayed at the reference location of the display by the reference standardized symbol display functionality.

* * * * *